(12) United States Patent
Blain et al.

(10) Patent No.: US 8,864,770 B2
(45) Date of Patent: Oct. 21, 2014

(54) OFFSET OPPOSING ARM SPINAL IMPLANT DISTRACTOR/INSERTER

(75) Inventors: Jason Blain, Encinitas, CA (US); Dean Johnson, Solana Beach, CA (US)

(73) Assignee: Spinal Elements, Inc., Carlsbad, CA (US)

(*) Notice: Subject to any disclaimer, the term of this patent is extended or adjusted under 35 U.S.C. 154(b) by 1255 days.

(21) Appl. No.: 12/047,178

(22) Filed: Mar. 12, 2008

(65) Prior Publication Data

US 2009/0234362 A1 Sep. 17, 2009

(51) Int. Cl.
*A61B 17/70* (2006.01)
*A61F 2/46* (2006.01)
*A61F 2/44* (2006.01)
*A61F 2/30* (2006.01)
*A61B 17/02* (2006.01)

(52) U.S. Cl.
CPC ..... *A61F 2/4455* (2013.01); *A61F 2002/30596* (2013.01); *A61F 2002/30784* (2013.01); *A61F 2002/30794* (2013.01); *A61F 2/4611* (2013.01); *A61F 2002/30904* (2013.01); *A61F 2002/30774* (2013.01); *A61F 2002/4628* (2013.01); *A61F 2002/4627* (2013.01); *A61B 2017/0256* (2013.01); *A61F 2002/30578* (2013.01); *A61B 17/7059* (2013.01)
USPC ............ 606/90; 606/99; 606/86 A

(58) Field of Classification Search
USPC ......... 606/86 A, 86 B, 90, 99, 105, 282, 914, 606/915, 279; 623/17.11, 908
See application file for complete search history.

(56) References Cited

U.S. PATENT DOCUMENTS

| | | | |
|---|---|---|---|
| 3,486,505 A | 12/1969 | Morrison | |
| 3,726,440 A * | 4/1973 | Deeb | 222/174 |
| 5,122,130 A | 6/1992 | Keller | |
| 5,235,966 A | 8/1993 | Jamner | |
| 5,431,658 A | 7/1995 | Moskovich | |
| 6,004,326 A | 12/1999 | Castro et al. | |
| 6,015,426 A | 1/2000 | Griffiths | |
| 6,096,038 A | 8/2000 | Michelson | |
| 6,179,873 B1 | 1/2001 | Zientek | |
| 6,224,599 B1 | 5/2001 | Baynham et al. | |
| 6,332,887 B1 | 12/2001 | Knox | |

(Continued)

OTHER PUBLICATIONS

Synthes Spine Brochure "Luminary™ Alif. Disc Preparation and implant insertion instruments," 2006.

*Primary Examiner* — David Isabella
*Assistant Examiner* — Suba Ganesan
(74) *Attorney, Agent, or Firm* — Knobbe, Marten, Olson & Bear, LLP

(57) ABSTRACT

Provided herein is a vertebral distractor-inserter comprising a pair of arms comprising a first arm having a proximal end and a distal end and a second arm having a proximal end and a distal end, wherein the distal end of the first opposing arm is laterally offset from the distal end of a second arm thereby comprising a pair of laterally offset opposing arms, a driving rod extending between the pair of laterally offset opposing arms, and a drive mechanism in mechanical communication with the driving rod. A vertebral distractor-inserter comprising a pair of opposing arms, a housing in mechanical communication with the arms and rotatable about an axis extending between the arms, and a driving rod extending through at least a portion of the housing and between the arms. A vertebral distractor-inserter adapted for single-handed use. A vertebral distractor-inserter having an implant depth adjustor. Methods for distracting adjacent vertebrae and inserting an implant using the device described herein.

23 Claims, 20 Drawing Sheets

(56) References Cited

U.S. PATENT DOCUMENTS

| | | |
|---|---|---|
| 6,478,800 B1 | 11/2002 | Fraser et al. |
| 6,652,533 B2 | 11/2003 | O'Neil |
| 6,752,832 B2 | 6/2004 | Neumann |
| 6,755,841 B2 | 6/2004 | Fraser et al. |
| 7,018,416 B2 | 3/2006 | Hanson et al. |
| 7,211,085 B2 | 5/2007 | Michelson |
| 7,722,622 B2 | 5/2010 | Evans et al. |
| 7,896,884 B2 | 3/2011 | Wing et al. |
| 8,062,304 B2 | 11/2011 | Blain et al. |
| 8,454,622 B2 | 6/2013 | Blain et al. |
| 8,551,105 B2 | 10/2013 | Blain et al. |
| 2002/0082695 A1 | 6/2002 | Neumann |
| 2002/0116009 A1 | 8/2002 | Fraser et al. |
| 2003/0028197 A1 | 2/2003 | Hanson et al. |
| 2003/0083747 A1* | 5/2003 | Winterbottom et al. ... 623/17.11 |
| 2003/0199874 A1 | 10/2003 | Michelson |
| 2004/0002758 A1 | 1/2004 | Landry et al. |
| 2004/0030387 A1 | 2/2004 | Landry et al. |
| 2004/0148029 A1 | 7/2004 | Bianchi et al. |
| 2004/0225295 A1 | 11/2004 | Zubok et al. |
| 2005/0071013 A1* | 3/2005 | Zubok et al. ............... 623/17.16 |
| 2005/0102029 A1 | 5/2005 | Blain |
| 2005/0107877 A1 | 5/2005 | Blain |
| 2005/0159818 A1 | 7/2005 | Blain |
| 2005/0165408 A1 | 7/2005 | Puno et al. |
| 2005/0177240 A1 | 8/2005 | Blain |
| 2005/0192574 A1 | 9/2005 | Blain |
| 2005/0192587 A1* | 9/2005 | Lim ................................ 606/86 |
| 2006/0074425 A1 | 4/2006 | Sutterlin et al. |
| 2006/0195097 A1 | 8/2006 | Evans et al. |
| 2006/0241641 A1 | 10/2006 | Albans et al. |
| 2006/0276801 A1* | 12/2006 | Yerby et al. ..................... 606/90 |
| 2007/0123903 A1 | 5/2007 | Raymond et al. |
| 2007/0123904 A1 | 5/2007 | Stad et al. |
| 2007/0233153 A1* | 10/2007 | Shipp et al. ..................... 606/99 |
| 2008/0161817 A1 | 7/2008 | Parsons et al. |

* cited by examiner

OFFSET OPPOSING ARM SPINAL IMPLANT DISTRACTOR/INSERTER

BACKGROUND OF THE INVENTION

Spinal disc replacement and/or spinal fusion are sometimes necessary for patients having lumbar degenerative disc disease. It has been estimated that at least 30% of people aged 30 to 50 will have some degree of disc space degeneration, although not all will have pain or ever be diagnosed formally with degenerative disc disease. After a patient reaches 60, it is more normal than not to have some level of disc degeneration. A twisting injury often starts degenerative disc disease, but it can also be initiated by everyday wear and tear on the spine.

Lower back pain is the most common symptom of a compromised disc emblematic of degenerative disc disease. For most patients with lumbar degenerative disc disease, the pain is for the most part tolerable and low-grade, but continuous with occasional flaring of intense pain. Pain can be simply centered on the lower back, or it can radiate to the hips and legs. It can get worse by sitting, or it can be intensified by twisting, lifting, or bending. For some, the pain from the disease decreases over time, since a fully degenerated disc has no pain-causing inflammatory proteins, and the disc usually collapses into a stable position, eliminating the micro-motion that often generates the pain.

For many, non-surgical care can successfully treat the symptoms associated with degenerative disc disease. Doctors will often prescribe a regimen of anti-inflammatory medication, pain medication (injected or oral), exercise, physical therapy, and/or chiropractic manipulation. For others, however, surgery is the best option for treatment once the non-surgical care has not resulted in relief and/or the patient's normal activities have been significantly constrained by his symptoms.

One option for surgical relief is lumbar spinal fusion surgery. This treatment stops motion at the painful segment of the spine by fusing two or more vertebrae. Depending on how many segments of the spine need fusion, and which specific spine segments are to be fused, this surgery may remove some of the normal motion of the spine. Additionally, where multiple segments are fused, back movement may be significantly diminished, and may itself cause pain (fusion disease). Nevertheless, single-level fusion at the L5-S1 segment—the most likely level to break down as a result of degenerative disc disease—does not significantly change the mechanics in the back and is the most common form of fusion. While lumbar spinal fusion surgery is major surgery, it can be an effective option for patients to enhance their activity level and overall quality of life, particularly when performed using minimally invasive techniques. However, while spinal fusion surgery has its benefits, and is effective in carefully selected patients, the cost of this success is the risk of accelerated degenerative change at adjacent segments.

Another, and increasingly more desirable, option to treat lumbar degenerative disc disease through surgery is disc replacement using an artificial disc. One potential benefit of disc replacement is the decreased risk of adjacent segment degeneration. It is postulated that replacing the disc, instead of fusing adjacent vertebrae together, maintains more of the normal motion of the lumbar spine, which in turn reduces the chance that adjacent levels of the spine will break down due to increased stress.

The standard surgical procedure for disc replacement approaches the cervical disc from the front (i.e. anterior approach). The entire worn-out disc is removed and a replacement disc is placed into the intervertebral disc space vacated by the removed, worn-out disc. One goal of this procedure is to retain as much normal motion as possible, while keeping the motion segment stable.

As currently practiced, disc replacement surgery and spinal fusion from the anterior approach require simultaneous use of multiple tools to keep the spine exposed, to prepare the site for implantation, to distract the vertebrae, and to implant the new disc or graft in the vertebral space at the proper orientation and to the desired depth. For example, several tools are often used to prepare the intervertebral space through removal of the cartilaginous endplates of the vertebral bodies. These tools may include rongeurs, rasps, and curettes. Another tool, such as a sizing gauge, might be used to determine the appropriate position and size of the implant to be used. Another tool is used to distract the vertebrae. While this distracting tool is holding the vertebrae apart, yet another tool may be used to place the implant in the distracted space. In some instances, a slap-hammer type tool, or an impact-type driver is used to place the implant between the vertebrae, or to prepare the intervertebral space for the implant.

SUMMARY OF THE INVENTION

The inventors have identified a need for improved tools to aid in disc replacement and/or spinal fusion. Such tools include implants and tools for placing such implants within the intervertebral space. In particular, the inventors have identified a need for an intervertebral implant that is adapted to limit the depth at which it is implanted between a pair of distracted vertebrae. The inventors have further identified a need for a spinal implant that is adapted to permit attachment of the implant to vertebral bone, particularly an exterior (e.g. anterior) surface of a vertebral bone. Having developed such an implant, the inventors have identified a need for a spinal implant distractor-inserter, which allow a spinal surgeon to more easily access and position a replacement disc or bone graft within the vertebral space. Furthermore, the inventors have identified a need for tools that are multifunctional and allow for single-handed operation to reduce the number of tools required for performing multiple functions during disc replacement surgery or during spinal fusion surgery and to improve the ease and speed with which disc replacement and/or spinal fusion can be completed.

The foregoing and additional needs are met by embodiments of the invention, which provide an intervertebral implant that is adapted to limit the depth at which it is implanted within the intervertebral space. In particular, the invention provides an implant having at least one means for contacting an anterior surface of a vertebral bone to limit the depth at which the implant is driven between distracted vertebrae. In some embodiments, such means for contacting the anterior surface of a vertebral bone comprises one or more flanges, which contact an anterior surface of a vertebral bone, thereby limiting the depth to which the implant may be inserted between the distracted vertebrae. In some embodiments, at least one flange possesses an aperture through which an attachment means may be inserted to fasten the implant to the vertebral bone. In some embodiments, the implant possesses two flanges, which are oriented in opposite directions. In some embodiments, the implant possesses two flanges, at least one of which, and in some embodiments both of which, possess an aperture. In some embodiments, an anterior (proximal) surface of the implant may possess one or more indentations for receiving a coupling mechanism at a distal end of a driving rod. In some embodiments, the implant may be textured on one or both horizontal surfaces. In some embodiments, such texturing may comprise transverse serrations, longitudinal serrations, cross-hatching, stippling or other texturing on one or both horizontal surfaces.

The foregoing and additional needs are met by embodiments of the invention, which provide a vertebral distractor-inserter (i.e. device), comprising a pair of arms having a first arm with a proximal end and a distal end, a second arm with a proximal end and a distal end, where the distal end of the first arm is laterally offset from the distal end of the second arm. The first and second arms thereby form a pair of laterally offset opposing arms. The vertebral distractor-inserter further comprises a driving rod extending between the pair of laterally offset opposing arms and a drive mechanism in mechanical communication with the driving rod. In some embodiments the vertebral distractor-inserter further comprises a housing. In such an embodiment, the housing is in mechanical communication with the pair of laterally offset opposing arms. The driving rod preferably extends through at least of portion of the housing. In some embodiments, the housing further consists of a handle attached to the housing. In some embodiments of the device, the drive mechanism consists of a ratchet drive mechanism. In an embodiment where a ratchet drive mechanism is used, the ratchet drive mechanism preferably consists of an activating lever mounted to the housing by an activating lever pivot, a driving rod with a set of ratchet teeth on the surface of the driving rod, a first ratchet pawl coupled to the activating lever and adapted to engage the set of ratchet teeth on the driving rod and move the driving rod distally relative to the housing, and a second ratchet pawl adapted to engage the set of ratchet teeth and oppose proximal motion of the driving rod relative to the housing. In some embodiments, the ratchet drive mechanism comprises an activating lever spring coupled to the activating lever and the handle, and wherein the activating lever spring opposes proximal movement of the lever relative to the handle. In some embodiments, the surface of the driving rod comprises an area that is substantially free of ratchet teeth on a contiguous lateral surface of the driving rod, and wherein the driving rod is movable proximally relative to the housing upon rotation of the rod about its axis such that the ratchet pawls are in contact with the contiguous lateral surface of the driving rod that is free of ratchet teeth. In an embodiment where the driving rod is substantially free of ratchet teeth, the ratchet teeth preferably disengage from the first and second ratchet pawls upon rotation of the driving rod about its axis. In some embodiments of the device, the driving rod comprises a proximal end where the proximal end of the driving rod has a driving rod handle. In some embodiments of the vertebral distractor-inserter device, the device is preferably designed and adapted for single hand use. The driving rod in some embodiments comprises a distal end and an implant interface that is coupled to, or part of, the distal end of the driving rod. In further embodiments an implant is preferably in contact with the implant interface. The distal motion of the driving rod imparts distal motion to the implant. The distal motion of the implant forces the laterally offset opposing arms apart. The laterally offset opposing arms of the distractor-inserter in some embodiments comprise an arm spring. In some embodiments, at least one of the offset opposing arms consists of a depth guard. In some embodiments, the implant interface consists of an implant coupler for attaching an implant. In some embodiments, the implant possesses at least one proximal flange. In some embodiments, the driving rod comprises a distal end having an implant interface, and the device comprises a housing, wherein the housing and at least a portion of the driving rod are rotatable relative to the pair of laterally offset opposing arms and the implant interface. In some embodiments, the implant interface preferably comprises an interface rotation element, whereby the interface rotation element allows rod rotation relative to the pair of laterally offset opposing arms. In some embodiments, the housing comprises a housing rotation element, whereby the housing rotation element allows the housing and rod to rotate relative to the pair of laterally offset opposing arms.

The device provided for herein further consists of a method for distracting adjacent vertebrae and for inserting an implant between the distracted vertebrae. The method includes the steps of mounting an implant to a driving rod of a vertebral distractor-inserter where the distractor-inserter consists of a pair of arms comprising a first arm having a proximal end and a distal end and a second arm having a proximal end and a distal end. The distal end of the first opposing arm of the vertebral distractor-inserter is laterally offset from the distal end of a second arm thereby forming a pair of laterally offset opposing arms. The method also includes positioning the distal ends of the pair of laterally offset opposing arms between the vertebrae to be distracted and actuating the driving rod to advance the implant between the two laterally offset opposing arms. Advancement of the implant between the arms forces the arms apart, resulting in distraction of the vertebrae by single-handed operation of the vertebral distractor inserter. As the vertebrae are distracted, the implant is inserted (implanted) between the distracted vertebrae by single-handed operation of the vertebral distractor-inserter. In some embodiments, the method provides for distracting adjacent vertebrae by activating the drive mechanism using one hand. The drive mechanism, when activated, moves the implant distally and distracts the pair of laterally offset opposing arms. The method further comprises in some embodiments advancing an implant between the distracted vertebrae wherein the advancing comprises activating the drive mechanism using one hand and extending the implant beyond the distal ends of the pair of laterally offset opposing arms. In some embodiments of the method for distracting adjacent vertebrae and inserting an implant between the distracted vertebrae, the distractor comprises a housing wherein the driving rod extends through at least a portion of the housing. In some embodiments, the implant is preferably a flanged implant.

Further provided herein is a method for distracting adjacent vertebrae and inserting an implant between the distracted vertebrae consisting of mounting the implant to a driving rod of a vertebral distractor-inserter, the vertebral distractor-inserter having a pair of arms comprising a first arm having a proximal end and a distal end and a second arm having a proximal end and a distal end, wherein the distal end of the first opposing arm is laterally offset from the distal end of a second arm. The device also comprises a ratchet drive mechanism in mechanical communication with the driving rod where the driving rod extends between the pair of laterally offset opposing arms. The method for distracting adjacent vertebrae and inserting an implant further comprises the step of positioning the distal ends of the pair of laterally offset opposing arms between the vertebrae. The method further consists of the step of distracting the vertebrae wherein the distracting step comprises activating the ratchet drive mechanism, which drives an implant located between the opposing arms distally. The implant forces apart the opposing arms, thereby imparting distracting force to the vertebrae. As the vertebrae are forced apart (distracted) the implant is inserted (implanted) between the distracted vertebrae. The implant is inserted until a flange located on a proximal end of the implant contacts an anterior surface of at least one of the distracted vertebrae, thereby stopping distal motion of the implant. In some embodiments, once the implant has ceased distal motion, further activation of the driving rod forces the distal ends of the opposed arms out of the intervertebral space. In some embodiments, the method of distracting adjacent vertebrae and inserting an implant between the distracted vertebrae consists of activating the ratchet drive mechanism of the vertebral distractor inserter comprises the step of ratcheting the driving rod distally, wherein the driving rod comprises an axis, a surface with a plurality of angled ratchet teeth on at least a portion of the surface. In such an embodiment, the ratchet drive mechanism comprises an activating lever capable of movement between a first position and a second position. The activating lever is mounted to the housing by an activating lever pivot. The drive mechanism further comprises a first ratchet pawl coupled to the activating lever. The first ratchet pawl is adapted to engage the ratchet teeth and move the driving rod distally relative to the housing. In some embodiments, the drive mechanism further comprises a second ratchet pawl adapted to engage the ratchet teeth and oppose proximal motion of the driving rod relative to the housing. In some embodiments, the method for distracting adjacent vertebrae and inserting an implant between the distracted vertebrae consist of a drive mechanism comprising a handle attached to the housing of the device and an activating lever spring coupled to the activating lever and the handle. The activating lever spring opposes proximal movement of the lever relative to the handle. In such an embodiment, the step of ratcheting further comprises the step of releasing the force on the activating lever and allowing the activating lever spring to move the activating lever toward the first position. In some embodiments, the method of distracting adjacent vertebrae and inserting an implant between the distracted vertebrae comprises the use of device with a pair of laterally offset opposing arms which comprise a depth guard and wherein the positioning of the pair of laterally offset opposing arms comprises urging the pair of arms between the vertebrae up to the position where the depth guard contacts the vertebrae. In some embodiments where the pair of arms comprises a pair of laterally offset opposing arms comprising a depth guard.

Further provided herein is a method for distracting adjacent vertebrae and inserting an implant between the distracted vertebrae comprises the steps of mounting the implant to a driving rod of a vertebral distractor-inserter having a pair of arms comprising a first arm having a proximal end and a distal end and a second arm having a proximal end and a distal end, wherein the distal end of the first opposing arm is laterally offset from the distal end of the second arm. The vertebral distractor-inserter further consists of a housing in mechanical communication with the pair of opposing arms which is rotatable about an axis extending between the opposing arms relative to the arms and to the implant. The distractor-inserter further comprises a drive mechanism in mechanical communication with the driving rod, wherein the driving rod extends through at least a portion of the housing and between the pair of laterally offset opposing arms and wherein at least a portion of the driving rod is rotatable about the axis extending between the pair of opposing arms relative to the pair of laterally offset opposing arms and to the implant. The method further comprises advancing the implant between the opposing arms, thereby distracting the vertebrae and inserting the implant between the distracted vertebrae. The implant is advanced until a flange on proximal end of the implant contacts an anterior surface of a vertebral bone, thereby stopping distal motion (advancement) of the implant. Once the implant is inserted, the pair of laterally offset opposing arms is retracted from between the vertebrae. In some embodiments, further actuation of the driving rod imparts force to the implant, whose further distal motion is impeded by the vertebral bone that it is abutting, which in turn forces the distal ends of the opposing arms out of the intervertebral space.

Also provided herein is a method of distracting adjacent vertebrae and inserting an implant between the distracted vertebrae comprising the steps of mounting the implant to driving rod of a vertebral distractor-inserter where the distractor-inserter has a pair of arms comprising a first arm having a proximal end and a distal end and a second arm having a proximal end and a distal end. The distal end of the first opposing arm is laterally offset from the distal end of the second arm. The method further consists of positioning the distal end of the pair of laterally offset opposing arms between the vertebrae up to the position where the depth guard contacts the vertebrae and distracting the vertebrae, inserting the implant between the distracted vertebrae and retracting the pair of laterally offset opposing arms from between the vertebrae. In some embodiments, the distracting step comprises activating the drive mechanism wherein the activating moves the implant distally and distracts the pair of laterally offset opposing arms. In some embodiments, the inserting step of the method comprises advancing the implant into the distracted space between the vertebrae. In some embodiments, the method for distracting adjacent vertebrae and inserting an implant between the distracted vertebrae comprises activating the drive mechanism and extending the implant beyond the distal ends of the pair of laterally offset opposing arms. In some embodiments activating the drive mechanism comprises the step of ratcheting the driving rod distally wherein the driving rod comprises an axis, a surface with a plurality of angled ratchet teeth on at least a portion of the surface. The drive mechanism comprises an activating lever capable of movement between a first position and a second position and mounted to the housing by an activating lever pivot. The mechanism also comprises a first ratchet pawl coupled to the activating lever and adapted to engage the ratchet teeth and move the driving rod distally relative to the housing, and a second ratchet pawl adapted to engage the ratchet teeth and oppose proximal motion of the driving rod relative to the housing. The method for distracting adjacent vertebrae and inserting an implant between the distracted vertebrae further comprises the ratcheting step wherein the ratcheting step comprises the step of applying a force to the activating lever to move the lever toward the second position. The method for distracting adjacent vertebrae and inserting an implant between the distracted vertebrae further consists of a handle attached to the housing of the distractor-inserter and an activating lever spring coupled to the activating lever handle, wherein the activating lever spring opposes proximal movement of the lever relative to the handle, and wherein the step of ratcheting further comprises the steps of releasing the force on the activating lever and allowing the activating lever spring to move the activating lever toward the first position.

Provided herein is a kit comprising a vertebral distractor-inserter, where the distractor-inserter has a pair of arms comprising a first arm having a proximal end and a distal end and a second arm having a proximal end and a distal end, and wherein the distal end of the first opposing arm is laterally offset from the distal end of the second arm. The vertebral distractor-inserter of the kit also comprises a driving rod extending between the pair of laterally offset opposing arms and a drive mechanism in mechanical communication with the driving rod. The kit also consists of a vertebral implant. In some embodiments, the kit further comprises a set of instructions. In some embodiments of the kit, the implant is adapted to be used with a vertebral distractor-inserter having laterally offset opposing arms. In some embodiments, the implant is a flanged implant.

Further provided for herein is a kit comprising a means for creating a space between two adjacent vertebrae, wherein the means for creating a space is capable of separating two adjacent vertebrae a desired distance from each other and a means for advancing a flanged implant into the space between the two vertebrae. The kit also consists of a flanged vertebral implant. In some embodiments, the kit further comprises a set of instructions.

Provided herein is a use of a vertebral distractor-inserter for the manufacturing of a kit adapted for inserting an implant between two adjacent spinal vertebrae wherein the kit comprises a vertebral distractor-inserter. The vertebral distractor-inserter consists of a pair of arms comprising a first arm having a proximal end and a distal end and a second arm having a proximal end and a distal end, wherein the distal end of the first opposing arm is laterally offset from the distal end of the second arm. The vertebral distractor-inserter also consists of a driving rod extending between the pair of laterally offset opposing arms, a drive mechanism in mechanical communication with the driving rod, and a flanged implant. In some embodiments of the use of a vertebral distractor-inserter for the manufacturing of a kit, the kit further comprises a set of instructions.

In some embodiments, there is further provided herein a kit comprising: (a) a vertebral distractor-inserter, comprising: (i) a pair of arms comprising a first arm having a proximal end and a distal end and a second arm having a proximal end and a distal end, wherein the distal end of the first opposing arm is laterally offset with respect to the distal end of a second arm, whereby the first arm and the second arms constitute a pair of laterally offset opposing arms; (ii) a driving rod extending between the pair of laterally offset opposing arms; and (iii) a drive mechanism in mechanical communication with the driving rod; and (b) a flanged vertebral implant. In some embodiments, the flanged vertebral implant comprises two flanges. In some embodiments, the flanged vertebral implant comprises at least one flange having an aperture therein. In some embodiments, the flanged vertebral implant comprises two flanges having an aperture in each.

In some embodiments, there is provided a vertebral implant comprising a proximal end and a distal end, said proximal end having at least one flange thereon. In some embodiments, the proximal end has two flanges. In some embodiments, one or both flanges have an aperture therein. In some embodiments, each flange has an aperture therein.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A is an illustration of a cutaway side view of one embodiment of the device in which the ratchet teeth of the driving rod have been engaged; FIG. 2B is an illustration of the housing of one embodiment of the device having ratchet teeth engaged by the drive mechanism wherein the activating lever is in a first position; FIG. 2C is an illustration of a cutaway side view of a housing of one embodiment of the device having ratchet teeth engaged by the drive mechanism wherein the activating lever is in a second position.

FIG. 3A illustrations a cutaway side view of one embodiment of the device having ratchet teeth disengaged for retraction of the driving rod; FIG. 3B provides a cutaway side view of the housing of one embodiment of the device having ratchet teeth disengaged for retraction of the driving rod.

FIG. 4A depicts a cut-away view of one embodiment of a non-ratcheting embodiment of the device; FIG. 4B depicts a cutaway side view of the housing of the non-ratcheting device.

FIG. 7A depicts one embodiment of the device where the vertebrae have been distracted in preparation for insertion of asymmetrical vertebral implant; FIG. 7B shows the device after the asymmetrical implant has been inserted and where the offset opposing arms are being retracted.

DETAILED DESCRIPTION OF THE INVENTION

The invention disclosed herein provides an intervertebral implant and a tool to aid in intervertebral disc insertion for use in intervertebral disc replacement and/or spinal fusion. The tool is a device that allows a spinal surgeon to more easily access and position a replacement disc or graft within the vertebral space. The implant is adapted to ensure that the implant does not exceed a predefined implantation depth, and in some embodiments to provide a means for attaching the implant to e.g. the vertebral body. In particular, the implant comprises a proximal end having at least one flange, which limits the distal progress of the implant as it is being advanced into the intervertebral space. The implant is designed so that when the implant has advanced to a predetermined depth into the intervertebral space, at least one flange makes contact with at least one vertebral body, thereby stopping advancement of the implant into the intervertebral space. Thus, the implant allows a spinal surgeon to control implantation depth of a replacement disc.

Additionally disclosed is a multifunctional device that is specially adapted to accommodate such an implant and, in at least some embodiments, permits substantially single-handed operation. Such a device reduces the number of tools required for performing multiple functions during disc replacement surgery and/or spinal fusion surgery, while freeing up an operator's other hand. In some embodiments, the tool (also referred to herein simply as a device), includes a driving rod that extends between a pair of laterally offset opposed arms where the ends of the opposed arms are laterally offset from each other. The lateral offset of the opposed arms accommodate an implant having at least one flange, in that the offset of a first arm allows the flange to occupy a space adjacent the first arm and opposite a second arm. An implant with one or more flanges having apertures therein may be desirable in situations wherein attachment of the implant to a surface of the vertebral bone, e.g. the vertebral body, for instance with screws, is desirable.

As used herein, the terms "intervertebral distractor-inserter," "distractor-inserter," and "device" may be taken to be interchangeable as used herein. The implant is any implant, whether wholly or partially artificial or natural, for insertion between adjacent vertebrae during spinal surgery.

The invention will be further described with reference to the appended drawings, which are intended to be illustrative of certain preferred embodiments of the invention, but are not intended to limit the scope of the invention. One of skill in the art will recognize that other embodiments of the invention are possible within the scope of the invention; and no such additional embodiment is intended by referring to the illustrative examples.

Figure 10:
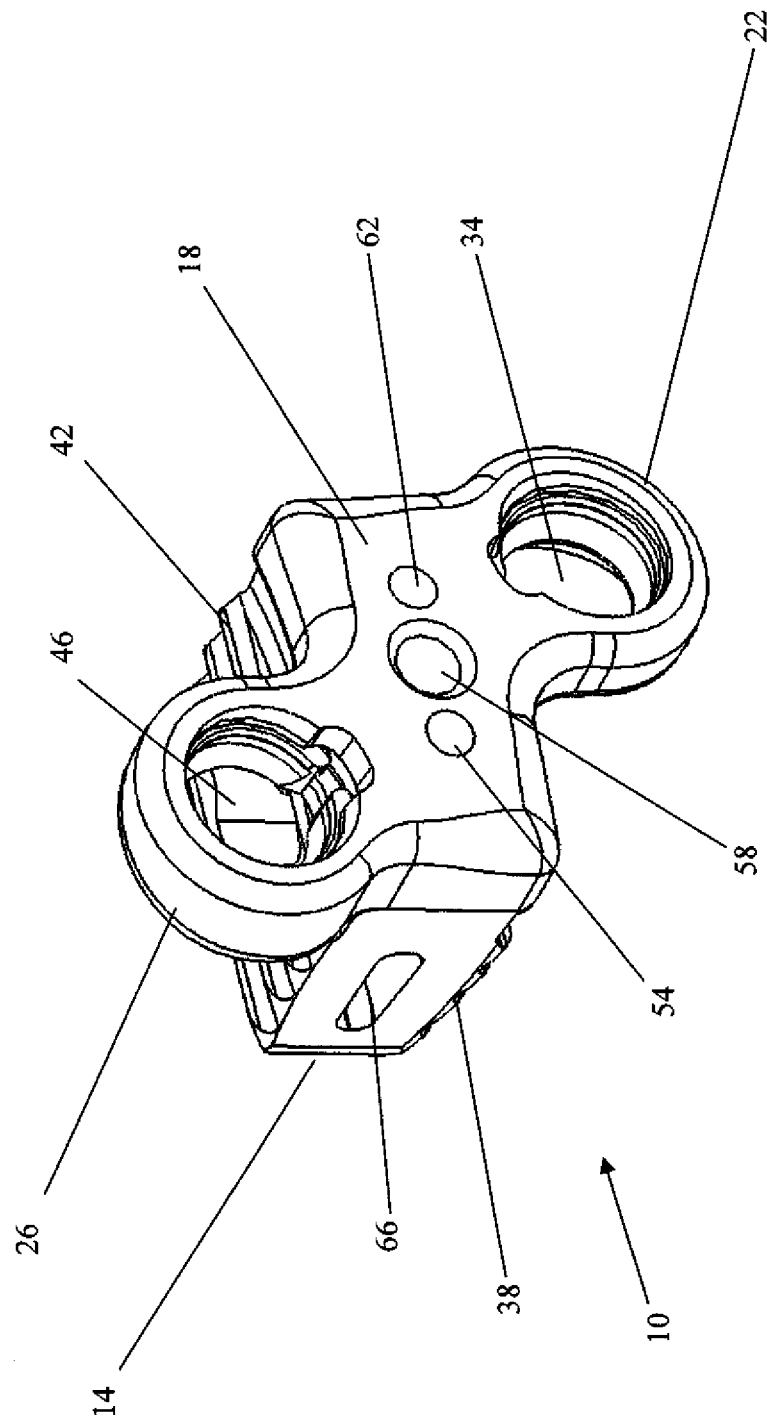
FIG. 10 is an illustration of an illustrative embodiment of an implant according to the present invention.

Attention is first directed to FIG. 10, which depicts a first, illustrative embodiment of an implant according to the present invention. The depicted implant 10 has a distal end 14 and a proximal end 18, a top surface 42 and a bottom surface 38. In the depicted embodiment, the top surface 42 is serrated with transverse serrations, as is the bottom surface 38. The proximal end has two flanges 22 and 26. The flange 26 projects upward and defines an aperture 46; the flange 22 projects downward and defines aperture 34. The proximal end also has indentations 54 and 62, which are adapted to engage a coupling member 140, described in more detail below. Additionally, in the depicted embodiments, the implant has a side aperture 66, which in some embodiments may have a matching side aperture on the opposite side. In some embodiments, the aperture 66 may continue all the way through to the other side of the implant 10. The top surface 42 and the bottom surface 38 may in some embodiments independently be smooth or stippled or may have transverse or longitudinal (proximal-to-distal running) serrations, or may have a criss-cross pattern. One surface may have a pattern different from the other pattern.

An implant according to the invention has at least one flange, and may have two or more flanges. Each flange projects in a direction, e.g. vertically (upward or downward, relative to the spine upon insertion) and upon insertion of implant between adjacent vertebrae to a predetermined maximal depth, abuts a vertebral body of a vertebra, thereby preventing movement of the implant beyond the predetermined maximal depth. Each flange may have an aperture for receiving a bone screw or other bone attachment device and affixing the implant in place. The implant may be made of any material, including any composite material, used for disc replacement and/or spinal fusion surgery.

Figure 1A:
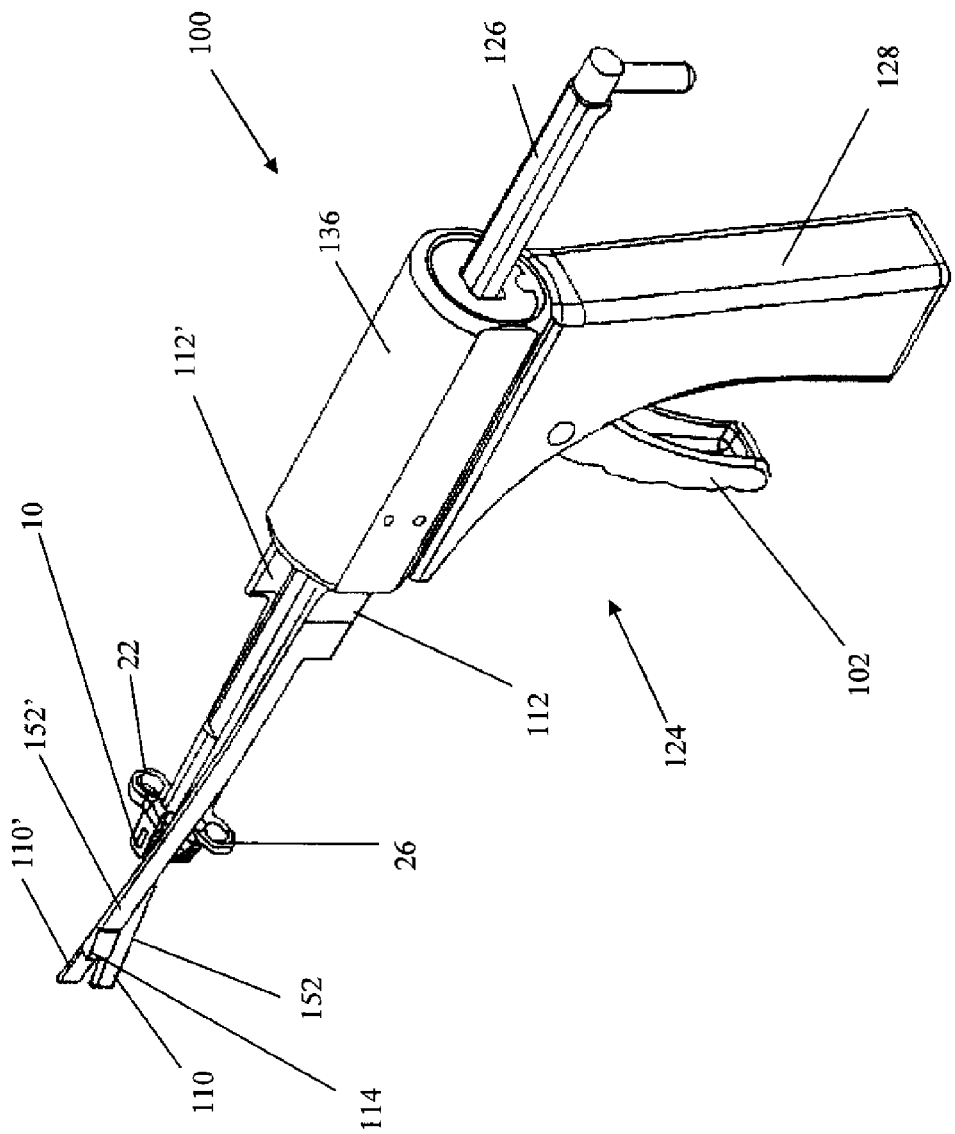
FIGS. 1A-1D are illustrations of external views of one embodiment of a device as viewed from different angles.

FIG. 1A depicts an external view of one illustrative embodiment of an inserter-distractor device 100. The embodiment of the device 100 depicted in FIG. 1A comprises a pair of laterally offset opposing arms 152, 152'. Arm 152 has a distal end 110 and a proximal end 112; and arm 152' has a distal end 110' and a proximal end 112'. The proximal ends 112, 112' are in mechanical communication with a housing 136. The distal ends 110, 110' of the pair of arms 152, 152' are laterally offset with respect to each other. In the embodiment shown in FIG. 1A, the arms are positioned such that the distal end 110' of the first arm 152' is positioned above the distal end 110 of the second arm 152; however in use, the device would be turned sideways so that the distal ends 110, 110' of the arms 152, 152' can be slipped between adjacent vertebra. Hence, the offset of the two arms 152, 152' is referred as a lateral offset, as the two arms 152, 152' are offset laterally with respect to the orientation of the spine in a disc replacement surgery. The offset of the distal ends 110, 110' of the pair of offset arms 152, 152' is sufficient to accommodate the flanges 22, 26 of the implant 10. The arms 152, 152' can be laterally offset by any amount suitable for accommodating the flanges 22, 26 of the implant 10. FIG. 1A further depicts an embodiment of the vertebral distractor-inserter 100 in which the proximal ends 112, 112' of the arms 152, 152' are in mechanical communication with a housing 136. A driving rod 126 extends through at least a portion of the housing 136 and between the laterally offset opposing arms 152, 152'. In some embodiments, the vertebral distractor-inserter 100 comprises a handle 128 attached to the housing 136. In some embodiments, the vertebral distractor-inserter 100 does not comprise a housing 136. In some embodiments, the housing 136 does not enclose the driving rod 126. In some embodiments, the rod 126 is external to, but in communication with, the housing 136.

FIG. 1A further depicts an embodiment having an activating lever 102 in mechanical communication with the driving rod 126. Movement of the activating lever 102 in the direction of the handle 128 causes the driving rod 126 to push the implant 10 distally toward the distal ends 110, 110' of the arms 152, 152'.

Figure 8A:
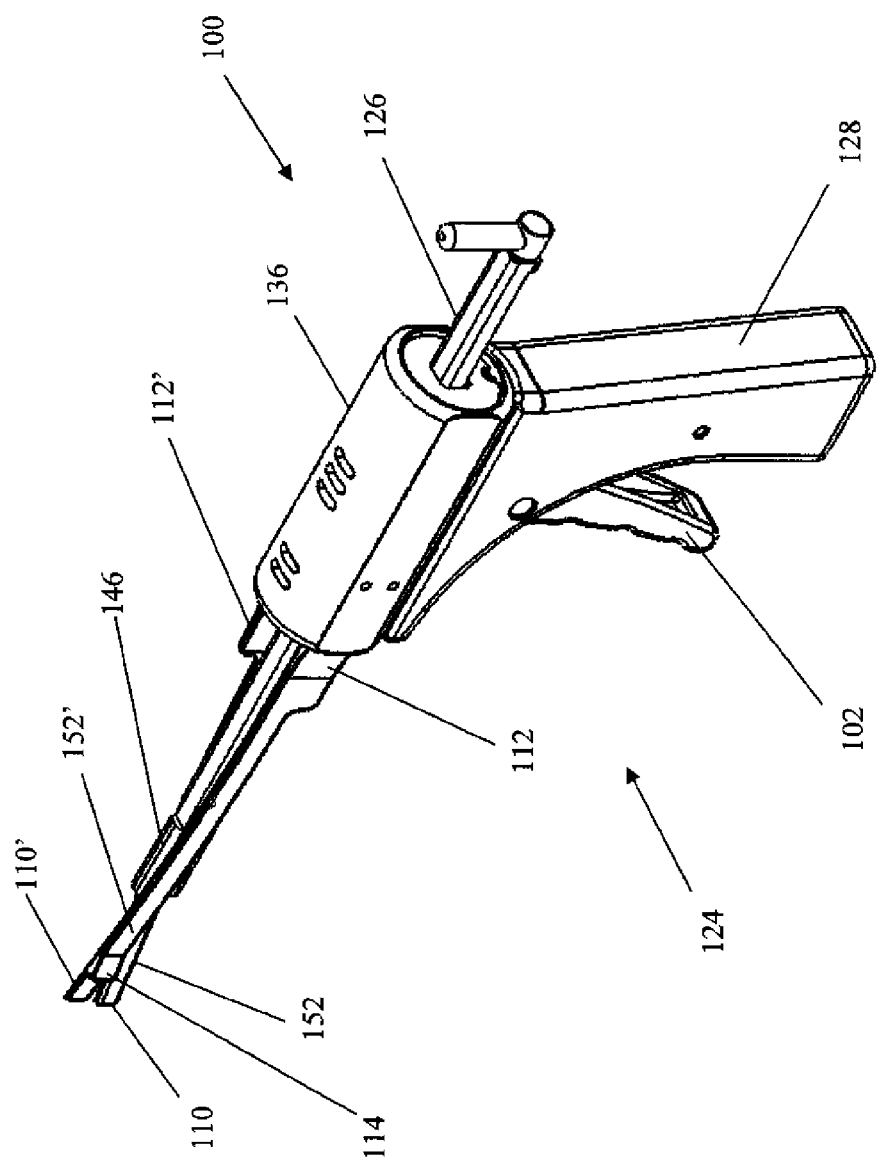
FIGS. 8A-8D are illustrations of external views of one embodiment of a device as viewed from different angles. The depicted device does not have an implant loaded between the opposing arms of the device.
Figure 8B:
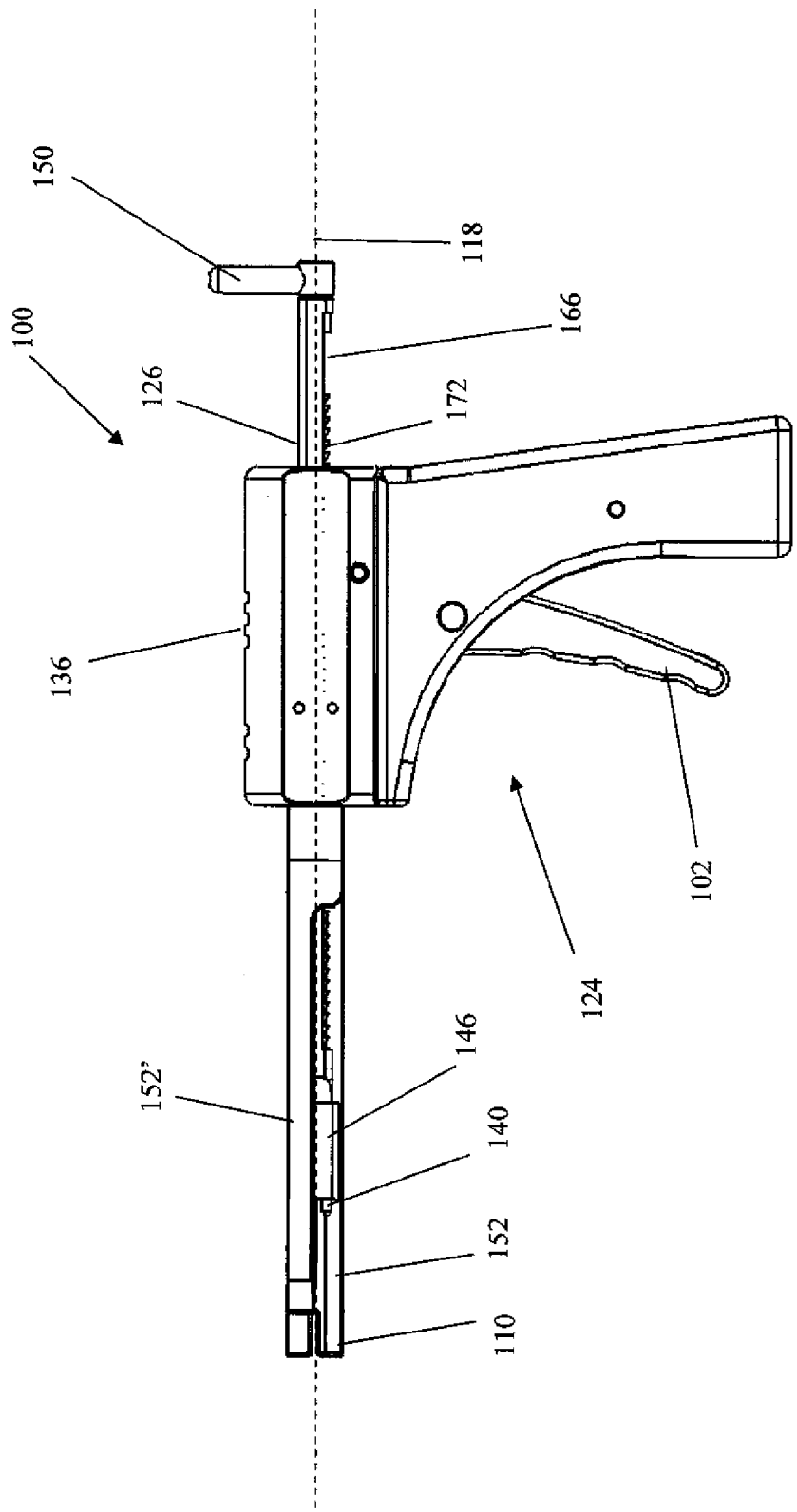
Figure 8C:
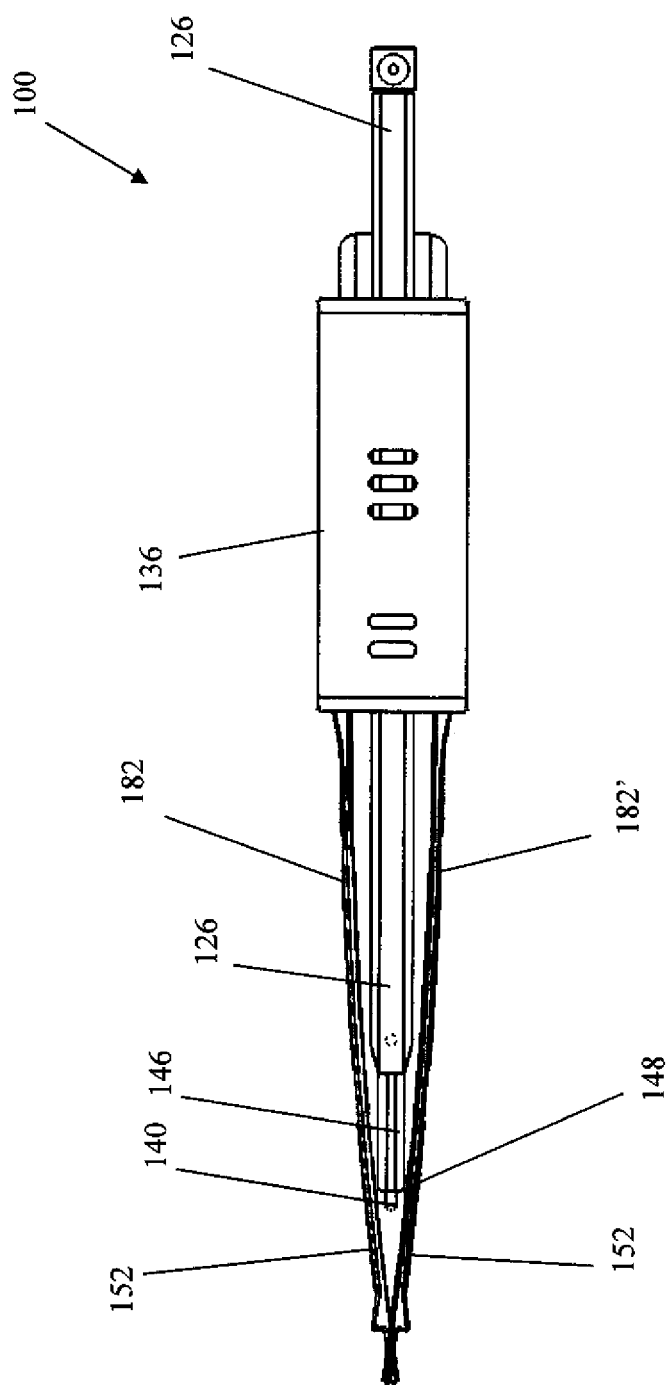
Figure 8D:
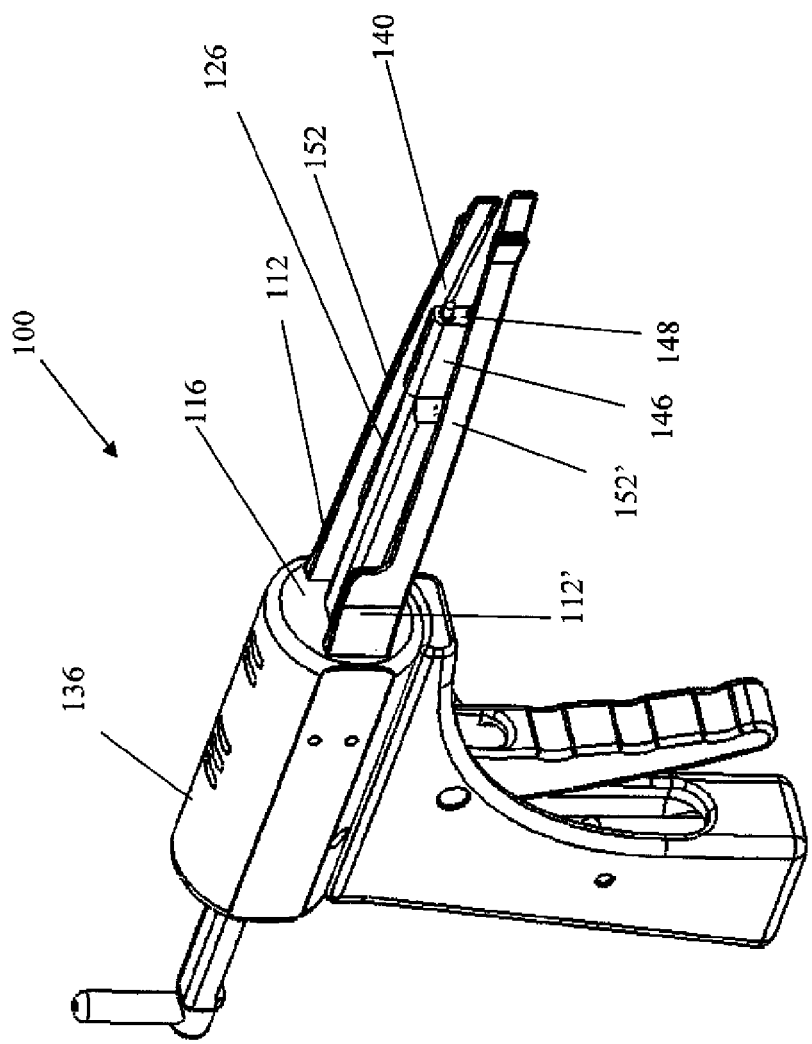

The embodiment shown has an implant coupler 146, which can be seen in FIGS. 8C and 8D. The implant coupler 146 has tines 140, which are adapted to be inserted into the indentations 54, 62 in the proximal end of the implant 10 as depicted in FIG. 10.

In some embodiments, the device 100 also has at least one depth guard 114 on at least one of the arms 152, 152'. The depth guard 114, which may be longitudinally adjustable, limits the depth to which the distal ends 110, 110' of the arms 152, 152' may penetrate into an intervertebral space. In some embodiments, the implant depth guard 114 is fixed relative to the implant coupler. In some embodiments, each arm 152, 152' has a depth guard 114 near its distal end 110, 110'.

FIG. 8A provides the same view of the device 100, but without an implant located between the arms 152, 152'. This view permits a clearer view of the coupler 146.

Figure 1B:
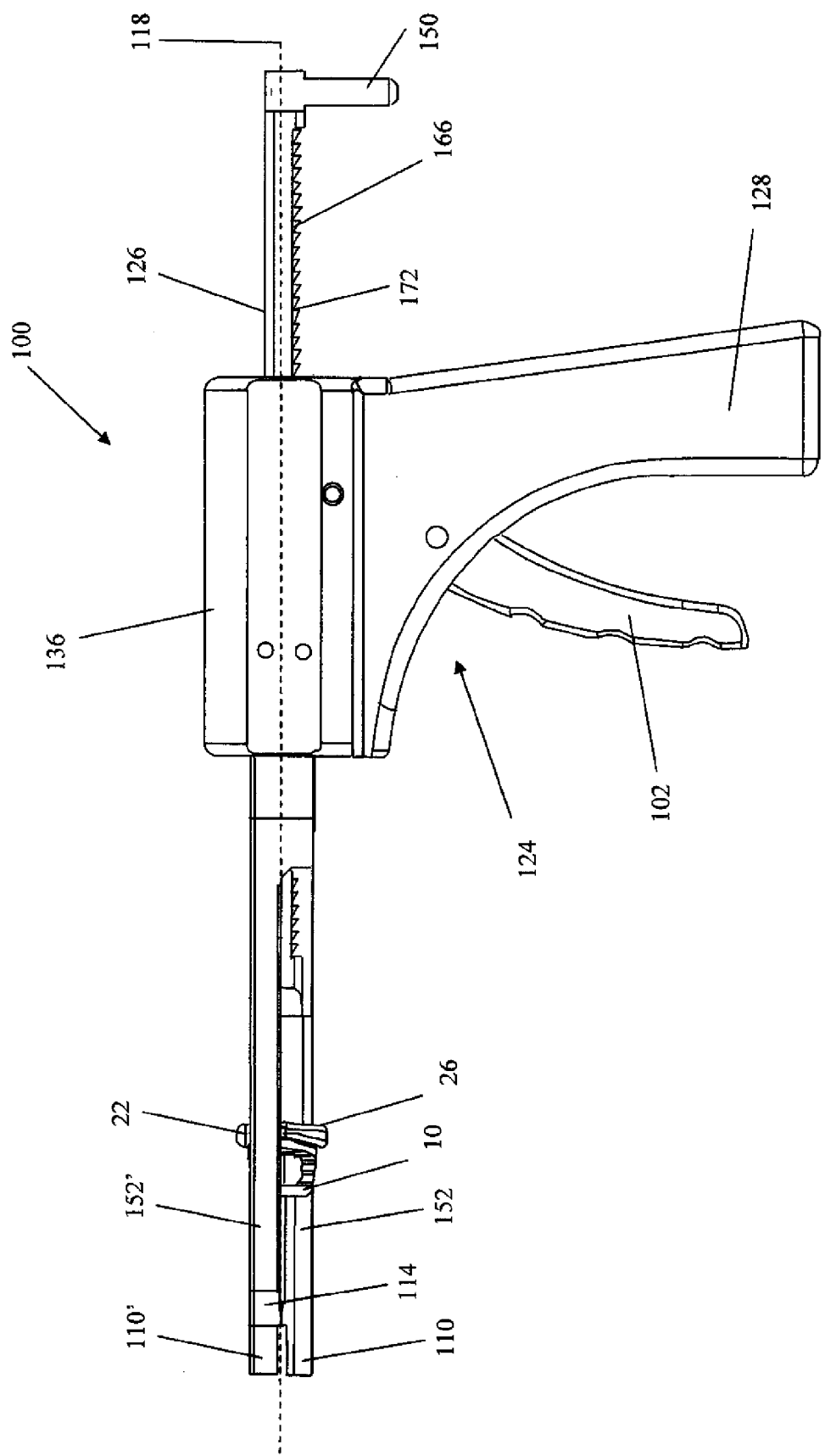

FIG. 1B depicts an external side view of one currently preferred embodiment of a vertebral distractor-inserter 100 comprising a housing 136, a pair of laterally offset opposing arms 152, 152' in mechanical communication with the housing 136, a driving rod 126 extending through at least a portion of the housing 136 and between the pair of laterally offset opposing arms 152, 152', wherein the driving rod 126 comprises an axis 118 and a surface 166 with a plurality of angled ratchet teeth 172 on at least a portion of the surface 166, and a ratchet drive mechanism 124 in mechanical communication with the driving rod 126. As previously mentioned, the mechanical communication may be effected through a number of means. In the depicted embodiment, the mechanical communication is through a ratcheting drive mechanism 124 within the housing 136. The ratcheting drive mechanism 124 uses ratchet teeth 172 to grip the driving rod 126 and drive the implant and the rod 126 distally when the activating lever 102 is moved toward the handle. The view also shows a driving rod handle 150 on the proximal end of the driving rod 126, discussed further below.

FIG. 8B depicts essentially the same view as FIG. 1B, except without the implant in place between the arms 152, 152'.

In both FIGS. 1B and 8B, the offset of arms 152, 152' can be envisioned as a distal end 110' of arm 152' extending the length of arm 152', above but not below the line 118, while an end 110 of arm 152 extends the length of the arm 152 below, but not above, line 118. This embodiment is especially suited for use with an implant 10 having two flanges 22, 26. In some embodiments, a flange may have only one flange. In such a case, an offset pair of arms could comprise a set of arms as depicted in the instant figures. However, it would also be possible for one of the arms to extend the full length of the arm both above and below line 118, while the other arm would extend the length of the arm only above or below the line 118. In other words, in some embodiments, the offset of one arm with respect to the other need not be complete, so long as at least one of the arms tapers or angles relative to the other arm such that a flange may be accommodated in the space created by the taper or angle.

Figure 1C:
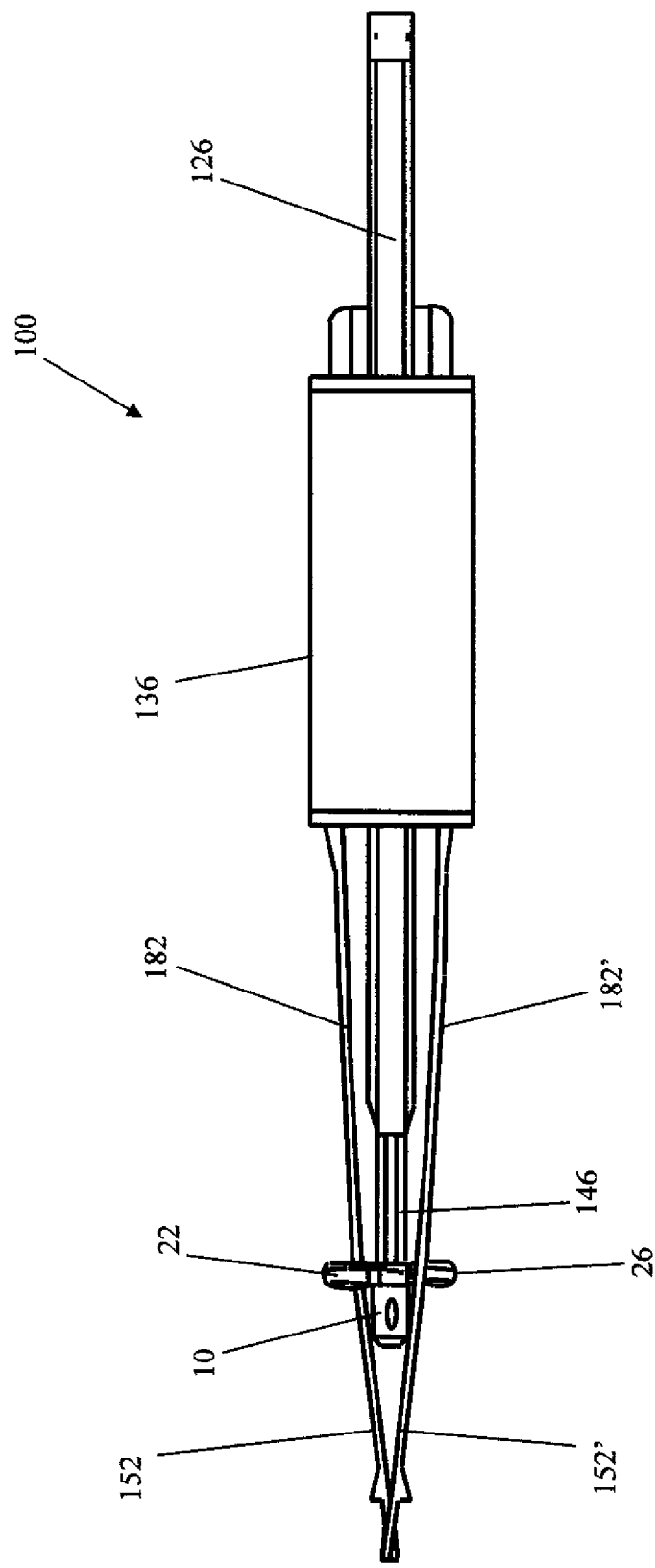

FIG. 1C depicts a top view of an embodiment of the device 100 with the implant coupler 146 in a partially retracted position. In this view, the housing 136 is shown along with the driving rod 126, which extends through the housing 136. Also visible is the implant 10, which travels along the medial (inner) edges 182, 182' of the arms 152, 152'.

FIG. 8C depicts substantially the same view as 1C, without the implant. Visible in this view are the coupler 146 and the tines 140, projecting from a distal end 148 of the coupler 146.

Figure 1D:
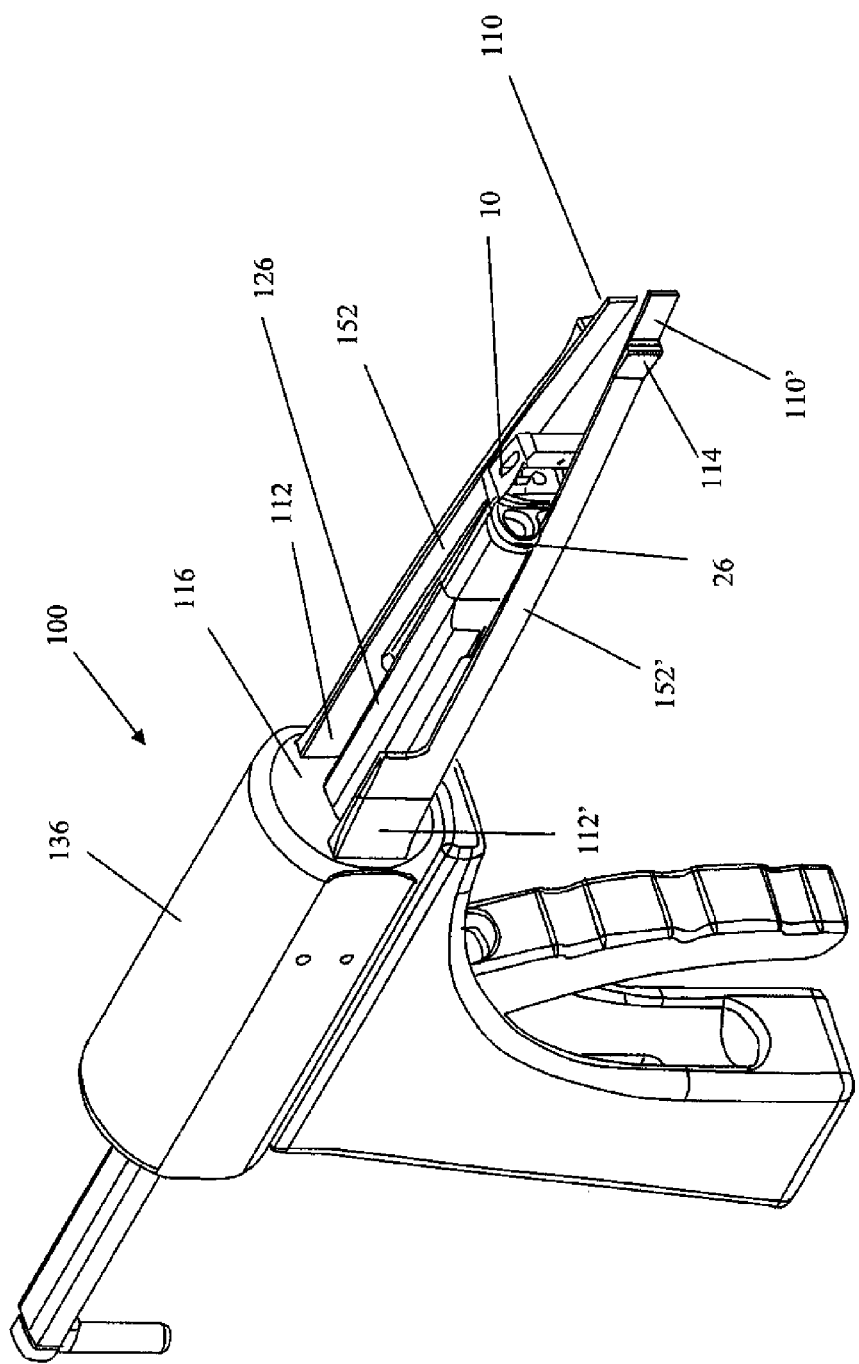

FIG. 1D depicts a forward view of the vertebral distractor-inserter in a partially retracted position as viewed from the top. The housing 136 has a distal end 116, to which the arms 152, 152' are attached, and about which the arms 152, 152' may, in some embodiments, be adapted to pivot. As the driving rod 126 is advanced distal to the housing 136, the implant 10 pushes apart the arms 152, 152', which in turn pivot at the distal end 116 of the housing 136. This allows the distal ends 110, 110' of the arms 152, 152' to distract vertebrae upon distal movement of the implant 10.

FIG. 8D depicts essentially the same view of the device 100, except that no implant is in place. This allows one to see the coupler 146 and the tines 140, which project from a distal end 148 of the coupler 146.

Figure 2A:
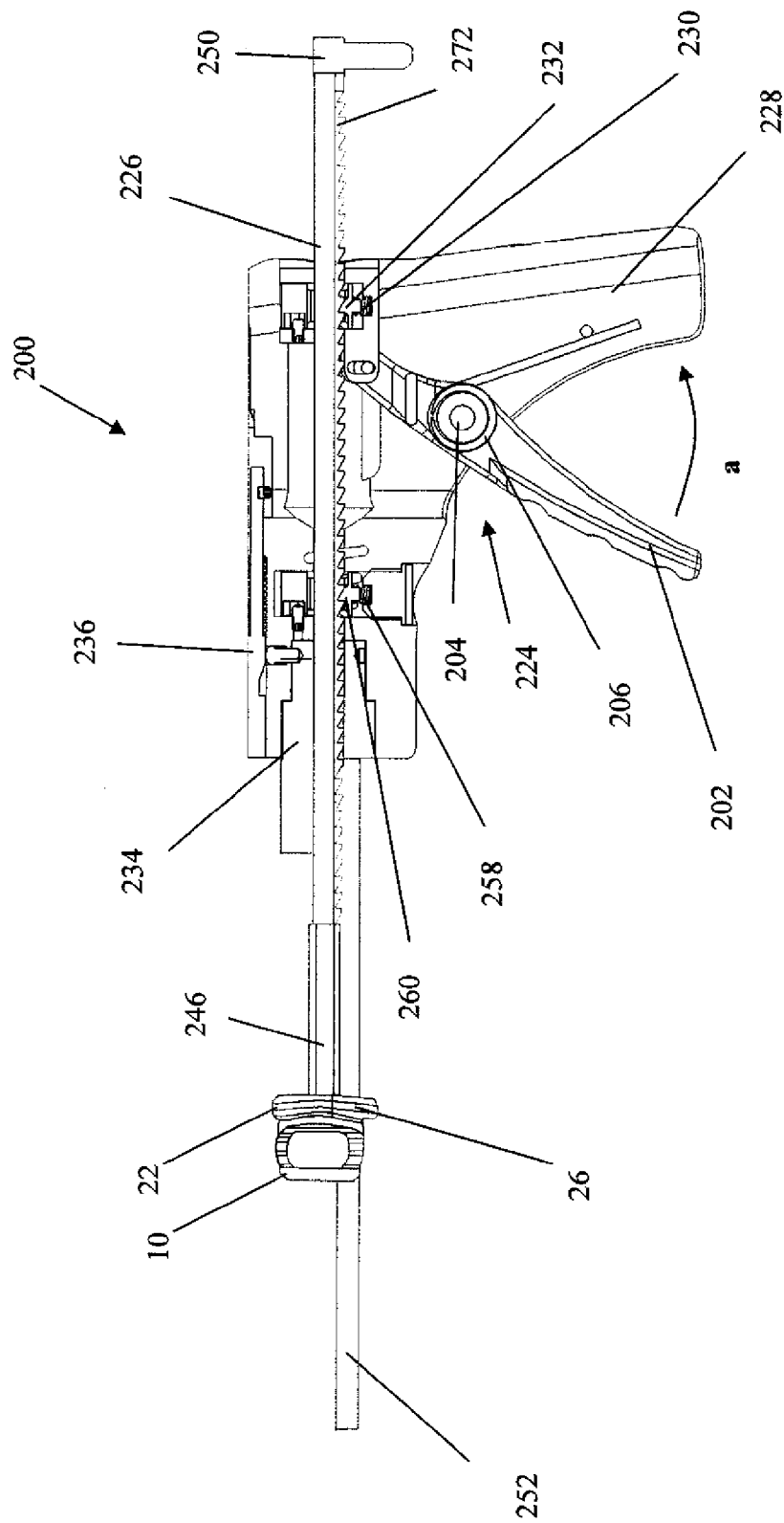
FIGS. 2A-2C depict cutaway side views of one embodiment of the device having ratchet teeth.

FIG. 2A shows a cutaway side view of an embodiment of a device 200 having ratchet teeth 272 engaged with ratchet pawls 232 and 260. A first ratchet pawl 232 and a first pawl spring 230, which work together with the activating lever 202, lever spring 206 and lever pivot point 204 to drive the driving rod 226 distally when the activating lever 202 is moved toward the handle 228 (i.e. in the direction of the arrow a of FIG. 2A. When the operator of the distractor-inserter uses the device, the operator grasps the handle 228 and the activating lever 202 in one hand and pulls the activating lever 202 proximally toward the handle 228. As the activating lever 202 is pulled toward the handle it pivots about the activating lever pivot 204, thereby moving the first ratchet pawl 232 distally. Since the first ratchet pawl 232 is engaged against the ratchet teeth 272 of the driving rod 226, the distal motion of the ratchet pawl 232 drives the driving rod 226 distally. Also depicted in this view is a second ratchet pawl 260 and a second pawl spring 258. The second ratchet pawl 260 cannot move distally or proximally, but the second ratchet spring 258 allows the second pawl to move away from the driving rod as each angled ratchet tooth 210 advances distally. Once each tooth 272 passes the second pawl 260, the pawl spring 258 pushes the second pawl 260 back toward the driving rod 226, to engage the next ratchet tooth 272 along the driving rod 226.

Thus the second ratchet pawl 260 allows distal motion of the driving rod 226 and prevents proximal motion of the driving rod 226. As the activating lever 202 is pulled again or farther toward the handle 228, further distal motion is imparted to the driving rod 226.

Thus, the second ratchet pawl 260 and the second pawl spring 258 cooperate to restrict or oppose proximal motion of the driving rod 226 as the activating lever 202 is reset away from the handle 228. In the depicted embodiment, the activating lever 202 has a spring 206 which biases the lever 202 toward the first position. Once the operator releases the force on the lever 202, the activating lever spring 206 moves the lever 202 away from the handle 228 toward its original position. As this occurs, the first pawl 232 and first pawl spring 230, linked to the activating lever 202, are also returned toward their original positions relative to the housing 236 prior to the operator pulling the lever 202 proximally. This occurs with no distal or proximal motion of the driving rod 226 since the first pawl spring 230 allows the first pawl 232 to move away and toward the driving rod 226 along the ratchet teeth 272 of the rod 226 as the pawl 232 ramps along the teeth 272 proximally. The second ratchet pawl 260, engaged against the ratchet teeth 272, opposes proximal motion of the rod 226 during this action. In embodiments where a gripping or other type of driving mechanism is used, the second ratcheting pawl 260 and spring 258 may be used to provide similar restricted proximal motion where the driving rod 226 comprises some ratchet teeth 272 on at least a portion of the rod 226 which can cooperate with the second ratchet pawl 260 and spring 258.

It is to be understood that the spring 206 may be eliminated in some embodiments and still provide substantially single handed operation. In such cases, the activating lever 202 will have to be moved toward the first position manually. This can be facilitated by including a closed handle (loop) similar to those common on scissors and forceps at the lower end of the activating lever 202, through which an operator may place her fingers and by means of which an operator can impart force to the lever 202 in either the direction away from or toward the handle 228 with a single hand.

In another embodiment, the device comprises a holding means wherein a second ratchet pawl and second ratchet spring are not present. The holding means instead may comprise, for example, a pneumatic grip, a hook, a latch, a grabbing device, the gripping mechanism described further herein, manually holding the driving rod in its distal position, or another mechanical means of restricting proximal motion.

In other embodiments, the device comprises a driving means comprising a first ratchet pawl and a spring that engages a thread which winds around the driving rod. Ratchet teeth may be unnecessary in this embodiment. The activating lever may instead drive the driving rod and implant distally by engaging the threads in the same ratcheting manner described herein, and retraction may be achieved by rotating the driving rod such that the rod moves proximally with the ratchet pawls engaged against the threads of the rod.

In other embodiments, the device comprises a driving means comprising for example, a pneumatic grip, a hook, a latch, a grabbing device, the gripping mechanism described further herein, an element adapted for manually pushing the driving rod distally, or another mechanical means of moving the rod and the implant distally to distract the arms and insert the implant. These and similar embodiments will be apparent to the person skilled in the art upon consideration of alternative embodiments described herein.

Further depicted in FIG. 2A is an implant 10, having flanges 22, 26, and an implant coupler 246, which are adapted to cooperate with the arms 252, 252' (not shown), the driving rod 226, such that the implant 10, in conjunction with the driving rod 226, distracts the arms 252, 252', which in turn distracts adjacent vertebrae, drives the implant distally, and places the implant within the intervertebral space between the two vertebrae. The flanges 22, 26 cooperate with the vertebral body of the vertebrae to limit the depth of penetration of the implant 10. Further depicted in this figure is a rotation element 234 which together allow the handle 228 to rotate relative to the arms 252 and 252', the driving rod 226, the implant interface 248, and the implant.

Figure 4A:
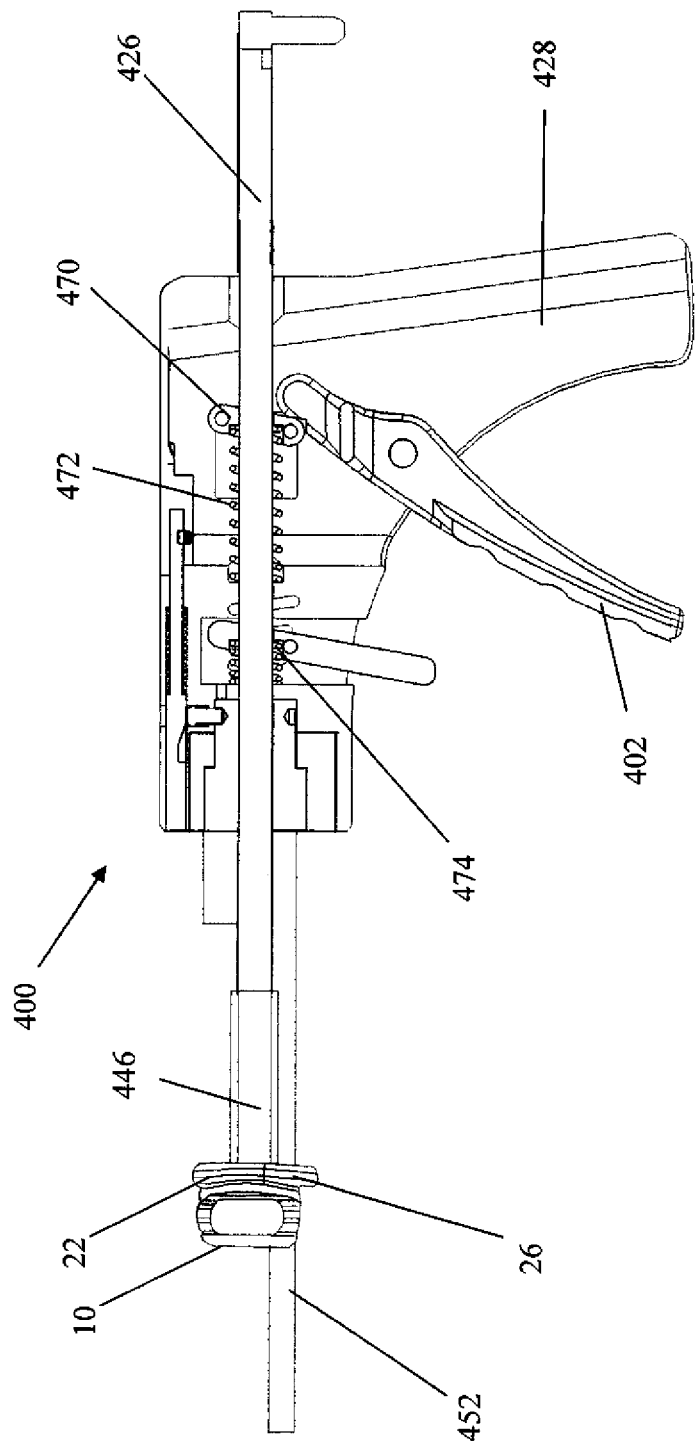
FIGS. 4A & 4B depicts cutaway side views of one embodiment of a non-ratcheting device.

In some embodiments, the vertebral distractor-inserter 200 comprises a ratchet drive mechanism 224, which comprises an activating lever 202 mounted to the housing 236 by an activating lever pivot 204, a first ratchet pawl 232 coupled to the activating lever 202 and adapted to engage the ratchet teeth 272 and move the driving rod 226 distally relative to the housing 236, and an engaging element to oppose proximal motion of the driving rod relative to the housing. The engaging element can be, for example, a gripping element 470 as shown in FIG. 4A, a grabbing element, a hooking element, a pressurized holding element; or it can be a manual pushing or holding element.

In some embodiments the ratchet drive mechanism 224 comprises an activating lever spring 206 coupled to the activating lever 202 and the handle 228, wherein the activating lever spring 206 opposes proximal movement of the lever 202 relative to the handle 228. In some embodiments of the distractor-inserter 200, the ratchet drive mechanism 224 comprises a first pawl spring 230 that opposes downward movement of the first pawl 232 and a second pawl spring 258 that opposes downward movement of the second pawl 260.

In some embodiments of the distractor-inserter 200, the driving rod 226 comprises a distal end and an implant coupler 146, coupled to the distal end of the driving rod 226. In some embodiments, the distractor-inserter 200 comprises an implant 10 in contact with the implant coupler 246, whereby distal motion of the driving rod 226 imparts distal motion to the implant through the implant coupler 246; and distal motion of the implant 10 in turn forces the offset opposing arms 252, 252' apart.

Figure 9:
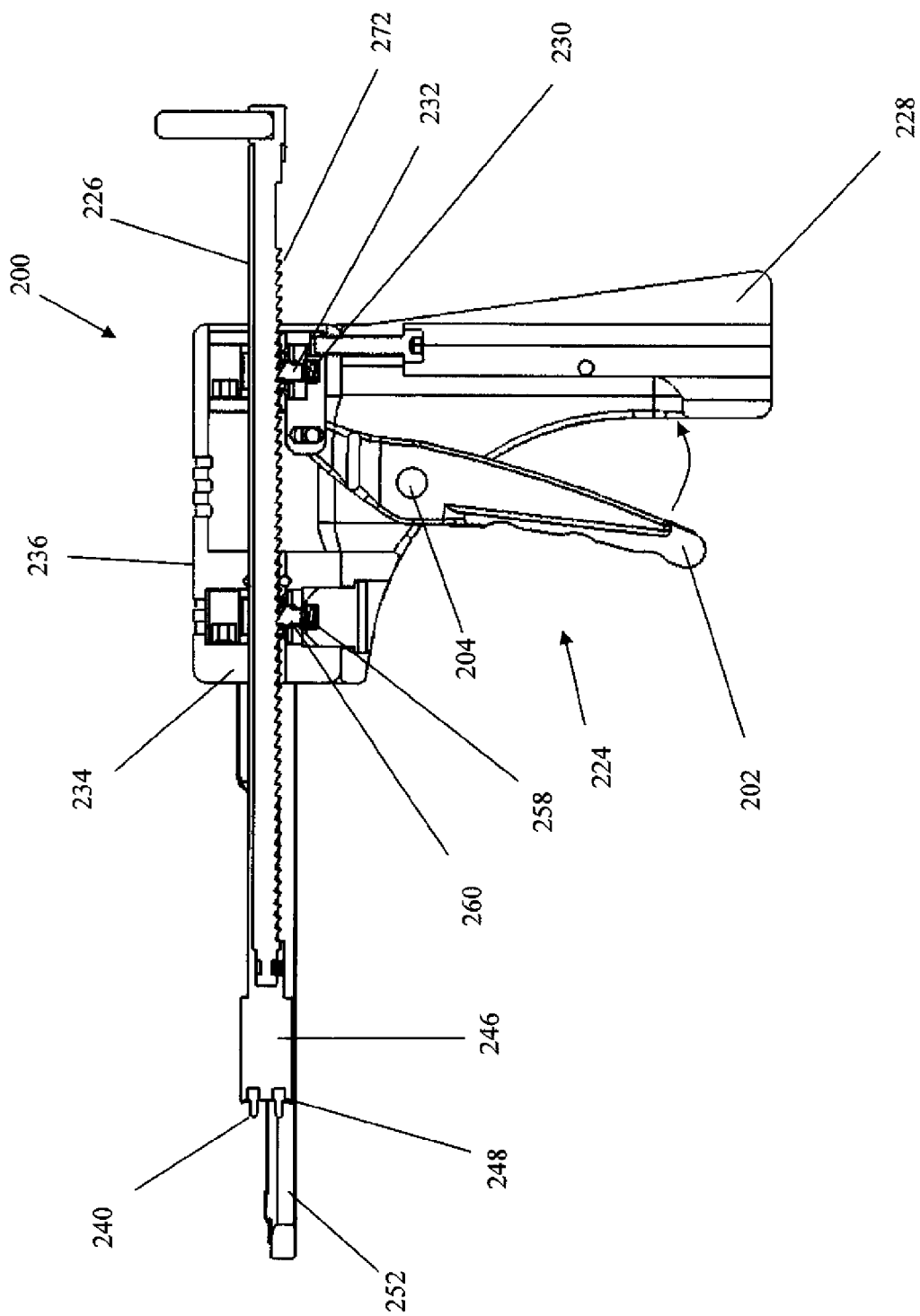
FIG. 9 is a cutaway illustration of a device according to the present invention, without an implant loaded between the opposing arms.

FIG. 9 depicts essentially the same view of the device 200 without the implant in place. In this view, the implant coupler 246 may be better envisioned. The implant coupler 246 has tines 240 projecting from a distal end 248 of the coupler 246.

Figure 2B:
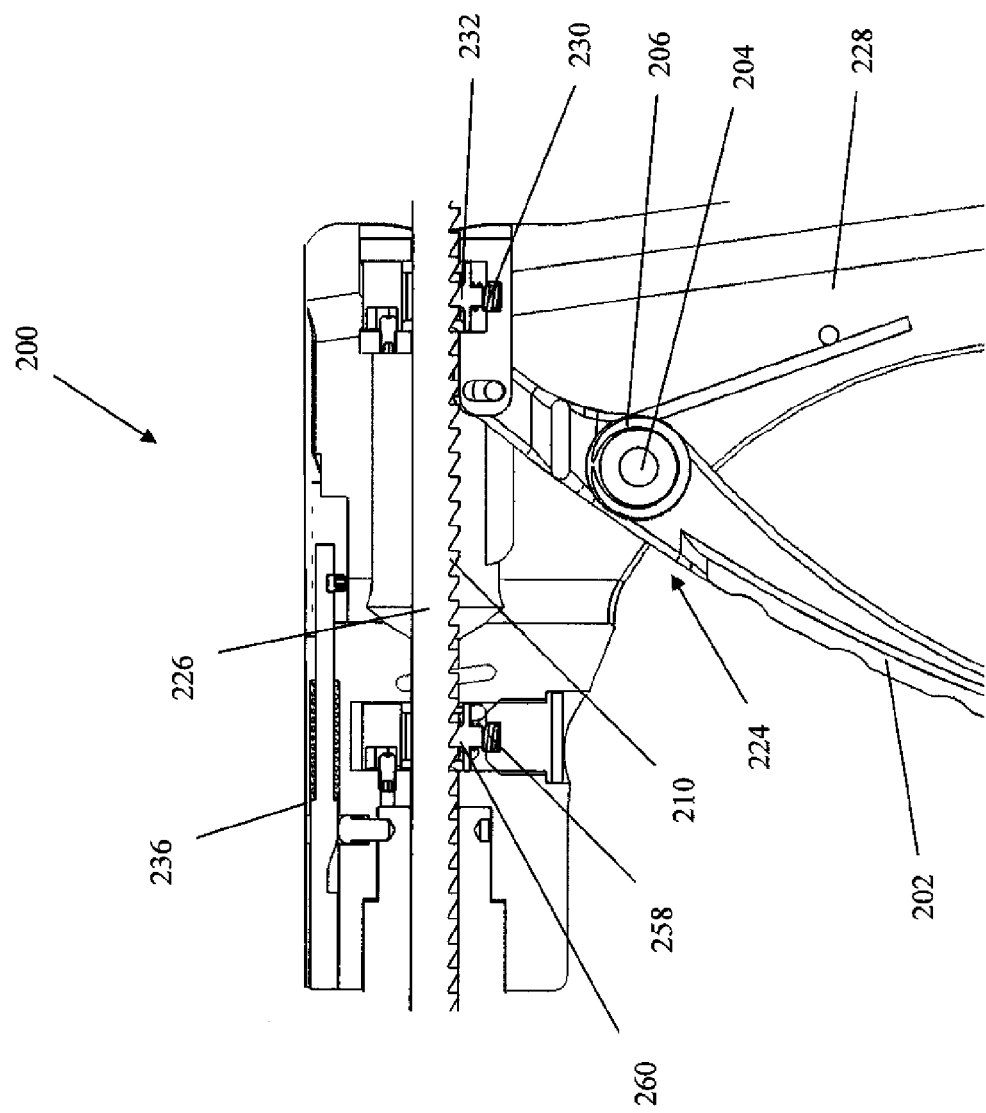

FIG. 2B shows a cutaway side view of the housing 236 of an embodiment of the device 200 having ratchet teeth 272 engaged by the drive mechanism 224 wherein the activating lever 202 is in a first position. A first ratchet pawl 232 engages the ratchet teeth 272 of the driving rod 226 and a first pawl spring 230 opposes motion of the first pawl 232 away from the driving rod 226 (downward, in the depicted embodiment, although, it could be in any direction away from the driving rod 226). Also shown is a second ratchet pawl 260. A second pawl spring 258 opposes motion of the second pawl 260 away from the driving rod 226 (downward, in this case, although it could be in any direction away from the driving rod 226). Further depicted is the activating lever pivot 204 about which the activating lever 202 pivots to drive the driving rod 226 and subsequently drives the implant distally by engaging and moving the ratchet teeth 272 distally when the activating lever 202 is moved toward the handle 228. Also depicted is the activating lever spring 206, which opposes activating lever 202 movement toward the handle 228, and which is capable of moving the activating lever 202 away from the handle 228 when the activating lever 202 is released.

Figure 2C:
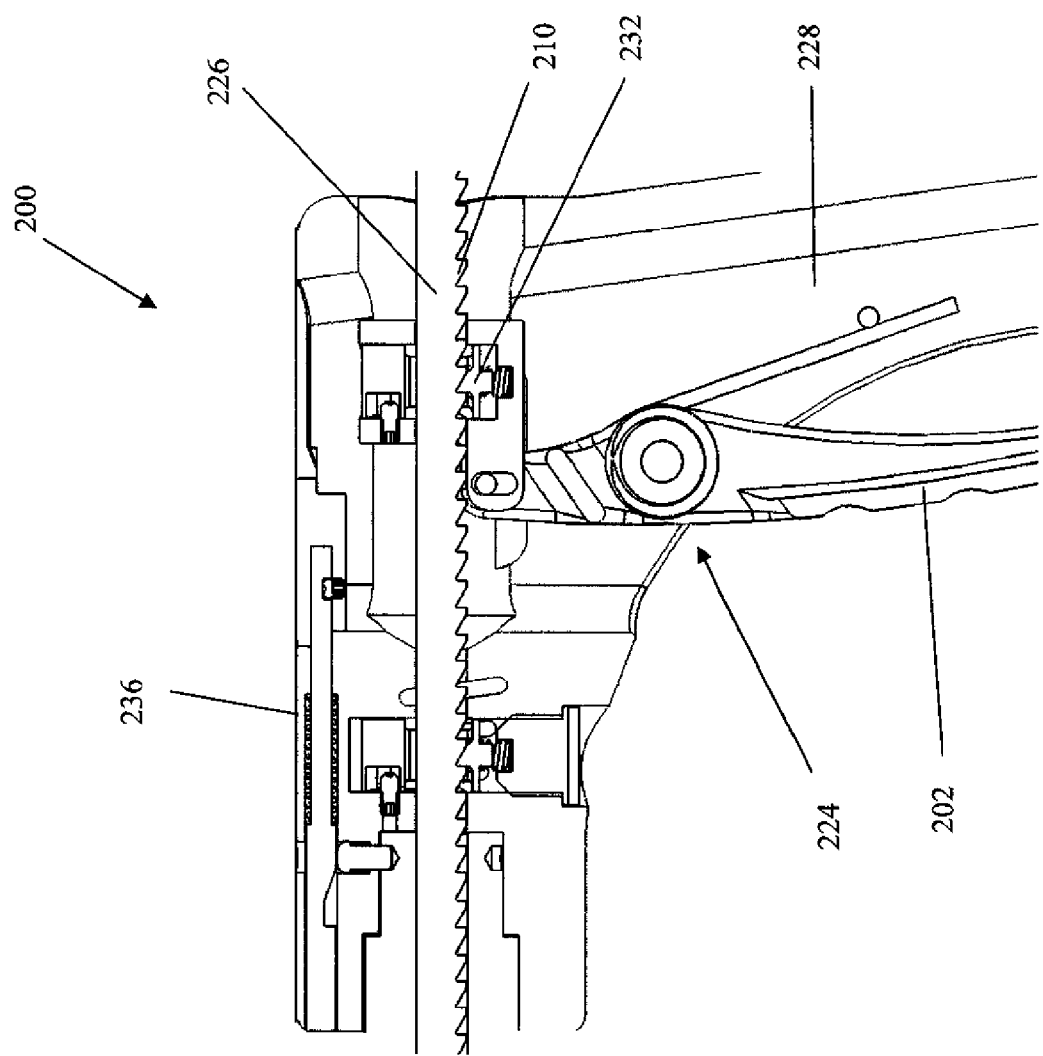

FIG. 2C shows a cutaway side view of the housing of an embodiment of the device 200 having ratchet teeth 272 engaged by the drive mechanism 224, wherein the activating lever 202 is in a second position after being moved toward the handle 228. The drive mechanism 224, the first ratchet pawl 232, and the driving rod 226 are shown in their respective positions when the activating lever 202 is moved toward the handle 228. As can be seen, movement of the activating lever 202 toward the handle 228 causes the first ratchet pawl 232 and the driving rod 226, through engagement of the ratchet pawl 232 with the ratchet teeth 272 of the driving rod 226, to move distally relative to the housing 236.

In some embodiments, the vertebral distractor-inserter 200 is adapted for single-handed use. In such an embodiment, the vertebral distractor-inserter 200 is adapted for substantially single-handed distraction of vertebrae and insertion of a vertebral implant.

It is to be understood in regard to the phrase "single-handed," the functions of holding the device in place and advancing the rod 226 and implant may in most instances be performed with a single hand. However, it is also noted that in some cases, depending upon operator preference and variations between patient physiology, two hands may be used, e.g. to impart greater force to the lever 202, without departing from the spirit and scope of the invention. The phrase "single-handed" thus distinguishes embodiments of the invention over distractor-inserter devices in which the device is held in place with one hand and the implant is advanced distally by twisting or striking an driving rod or other implant driving means. It is considered that whether used with one hand or two, the device of the present invention provides force to both advance the implant and distract the arms of the device, thereby distracting adjacent vertebrae. In currently preferred embodiments, the device of the present invention also permits the operator to hold the device in place and impart force for distraction and insertion with a single hand. In addition to the aforementioned advantages, single handed use is amenable to less invasive surgery than two-handed use.

Figure 3A:
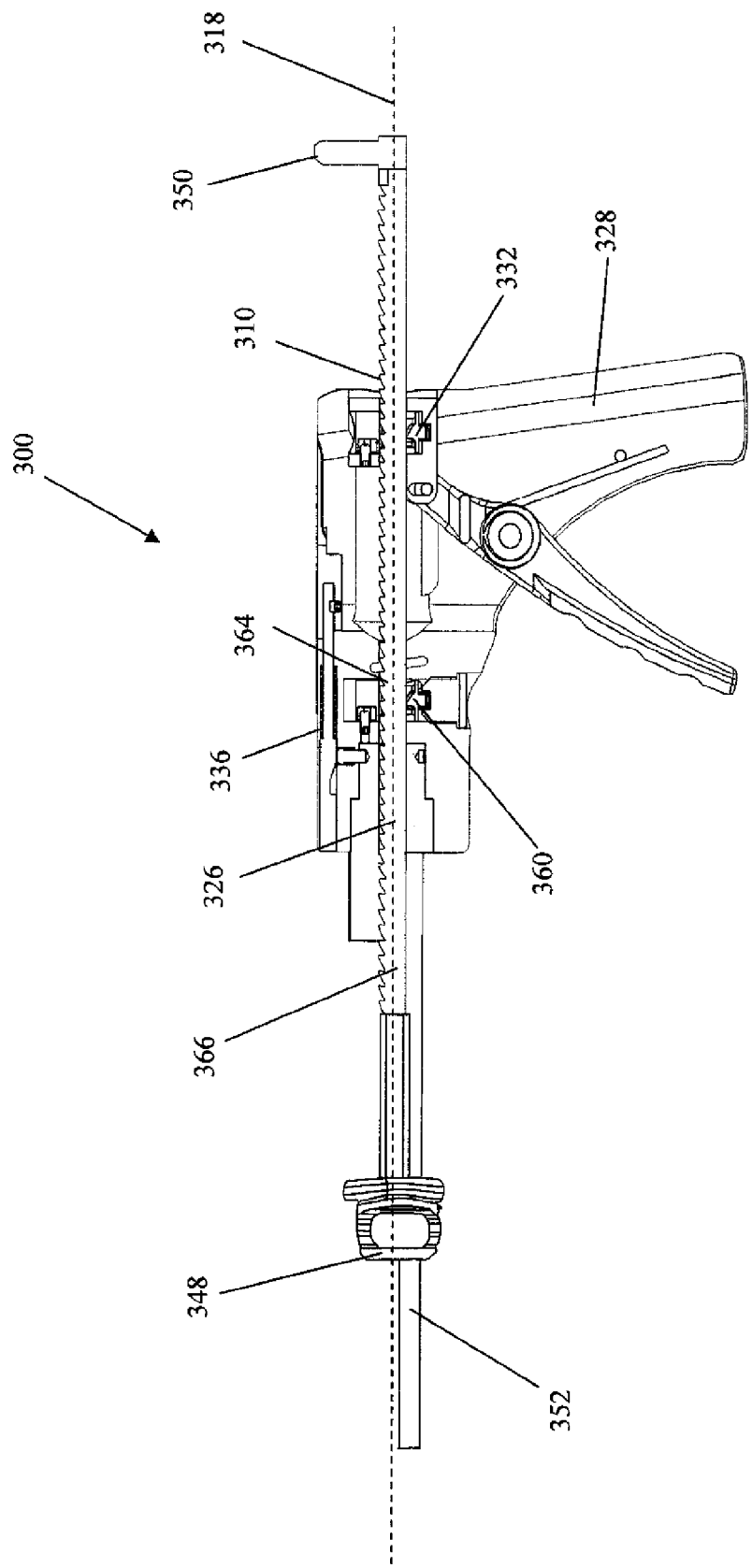
FIGS. 3A & 3B depict cutaway side views of one embodiment of a ratcheting device in which the ratcheting teeth are disengaged.

Some embodiments of the device are adapted to allow retraction of the implant interface and the driving rod relative to the arms of the device. This may be achieved in a number of ways. In the embodiment of the device 300 depicted in FIG. 3A, a cutaway side view of the device 300 is shown having ratchet teeth 372 disengaged for retraction of the driving rod 326. The driving rod of this embodiment has a surface 366 comprising a substantially smooth area 364 and ratchet teeth 372. When the driving rod 326 handle 350 is turned about its axis 318, for example with the driving rod handle 350, such that the ratchet teeth 372 are no longer engaged by the ratchet pawl 332, or the ratchet pawls 332, 360 if there are two, the driving rod 326 is free to be moved proximally (retracted) relative to the housing 336 and the arms 352. Although this action is favorably carried out by the operator holding the handle 328 in one hand and turning the driving rod handle 350 with the other, this action is not to be interpreted as derogating in any way single-handed operation of the device 300, as single-handed operation generally refers to simultaneously holding the handle 328 and imparting drive force to the driving rod 326 with a single hand. As the driving rod 326 may be easily disengaged from the pawls 332, 360 with, for example, a single 180° twist about its axis 318, it is considered that the present invention provides for easier and faster retraction of the driving arm 326 than is provided by previously known devices that require screwing the arm backwards.

In another embodiment, the driving rod 326 may comprise a threading around the driving rod instead of ratchet teeth, wherein the ratchet pawl 332 or ratchet pawls 332, 360 if there are two, may engage the threads instead of ratchet teeth. To retract the driving rod 326, rather than turning the driving rod 326 until the pawl(s) 332, 360 disengages the teeth, and then pulling the driving rod 326 proximally, the driving rod 326 and, thereby, the implant interface 348, may be retracted by turning the driving rod 326 around the long axis 318 of the rod 326. In this embodiment, the rod threads are not disengaged from at least the first ratchet pawl 332.

Other embodiments may comprise combinations of threads, ratchet teeth 372, and/or a substantially smooth area 364 along the driving rod surface 366, and a combination of ratcheting and gripping elements to provide the controlled distal and proximal movement of the driving rod 326, the implant, and implant interface 348 relative to the arms 352, 352', and to the housing 336.

Figure 3B:
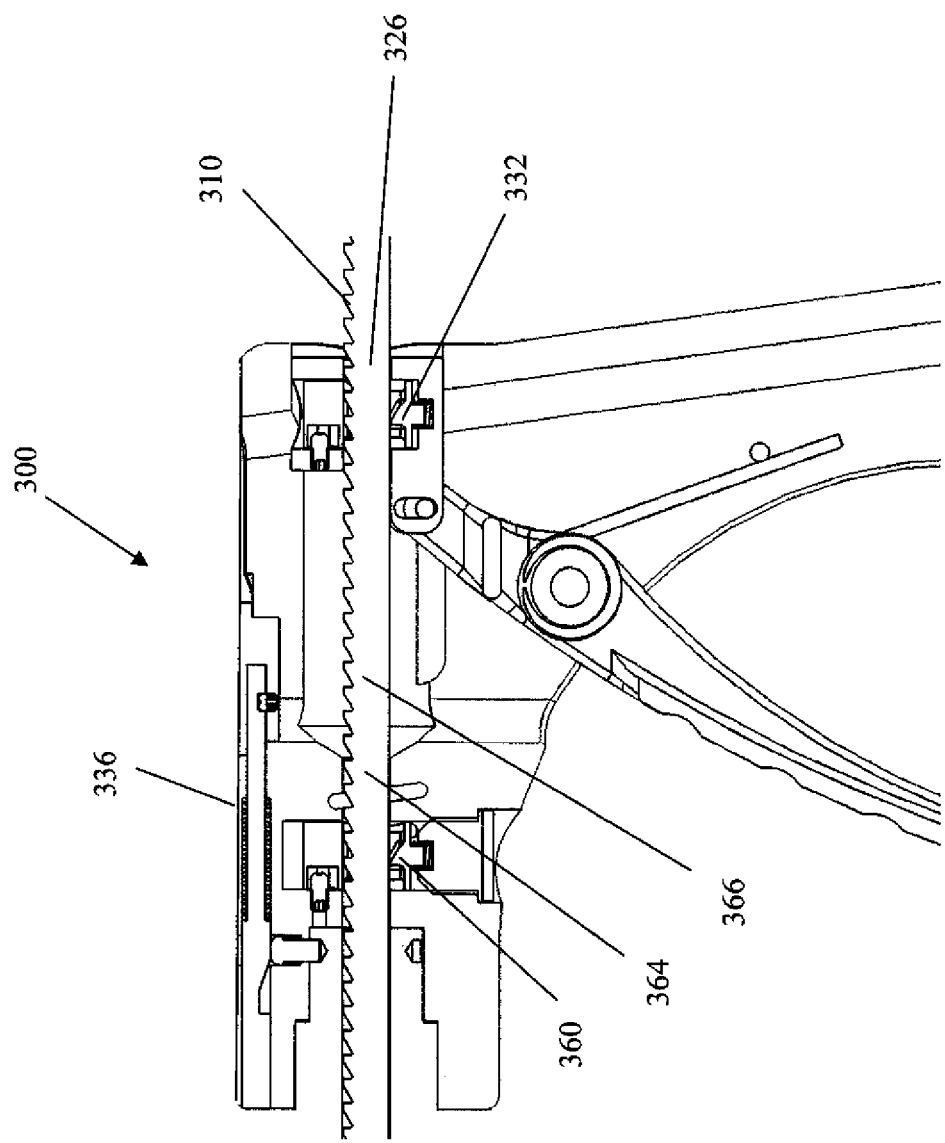

Likewise, the embodiment of FIG. 3B shows a cutaway side view the housing 336 of an embodiment of the device 300 having ratchet teeth 372 of the driving rod 326 disengaged from the first ratchet pawl 332 and second ratchet pawl 360 for retraction of the driving rod 326. Also shown is the substantially smooth area 364 of the driving rod 326 surface 366 which allows proximal retraction of the driving rod 326 and, thereby, the implant interface 348.

In some embodiments, the ratchet teeth 372 extend along the driving rod 326 a length sufficient to allow the offset opposing arms 352, 352' to meet at the midline of the device when the implant is loaded prior to distraction and to allow the implant to be inserted between the vertebrae.

In some embodiments, the surface 366 of the driving rod 326 comprises an area 364 that is substantially free of ratchet teeth on a contiguous lateral surface 366 of the driving rod, and the driving rod 326 is movable proximally relative to the housing 336 upon rotation of the rod 326 about its axis 318 such that the ratchet pawls 332, 360 are in contact with the contiguous lateral surface 366 that is free of ratchet teeth 372. In some embodiments, the ratchet teeth 312 disengage from first and second ratchet pawls 332, 360 upon rotation of the driving rod 326 about its axis 318. In some embodiments, the driving rod 326 comprises a proximal end having a handle 350.

FIG. 4A shows a non-ratcheting embodiment of the device 400. The device 400 has a pair of offset opposing arms (of which only one 452 is shown) and two gripping elements 470, 474, wherein the first gripping element 470 is adapted to grip and drive the driving rod 426 distally when the activating lever 402 is moved toward the handle 428. The second gripping element 474 allows distal movement of the driving rod 426, but opposes proximal motion of the driving rod 426 when the activating lever 402 is released and allowed to move away from the handle 428, for example, to its original resting (first) position. The first gripping element 470 also releases its grip on the driving rod 426 when the lever 402 is moved away from the handle 428, for example, to its original resting position. The first gripping spring 472 moves the first gripping element 470 proximally when the activating lever 402 is released. The first gripping element 470 is adapted to only grip the driving rod 426 upon distal motion of the driving rod. Similarly, in the embodiment of FIG. 4A, the second gripping element 474 is adapted to only grip the driving rod 426 upon proximal motion of the driving rod.

Figure 4B:
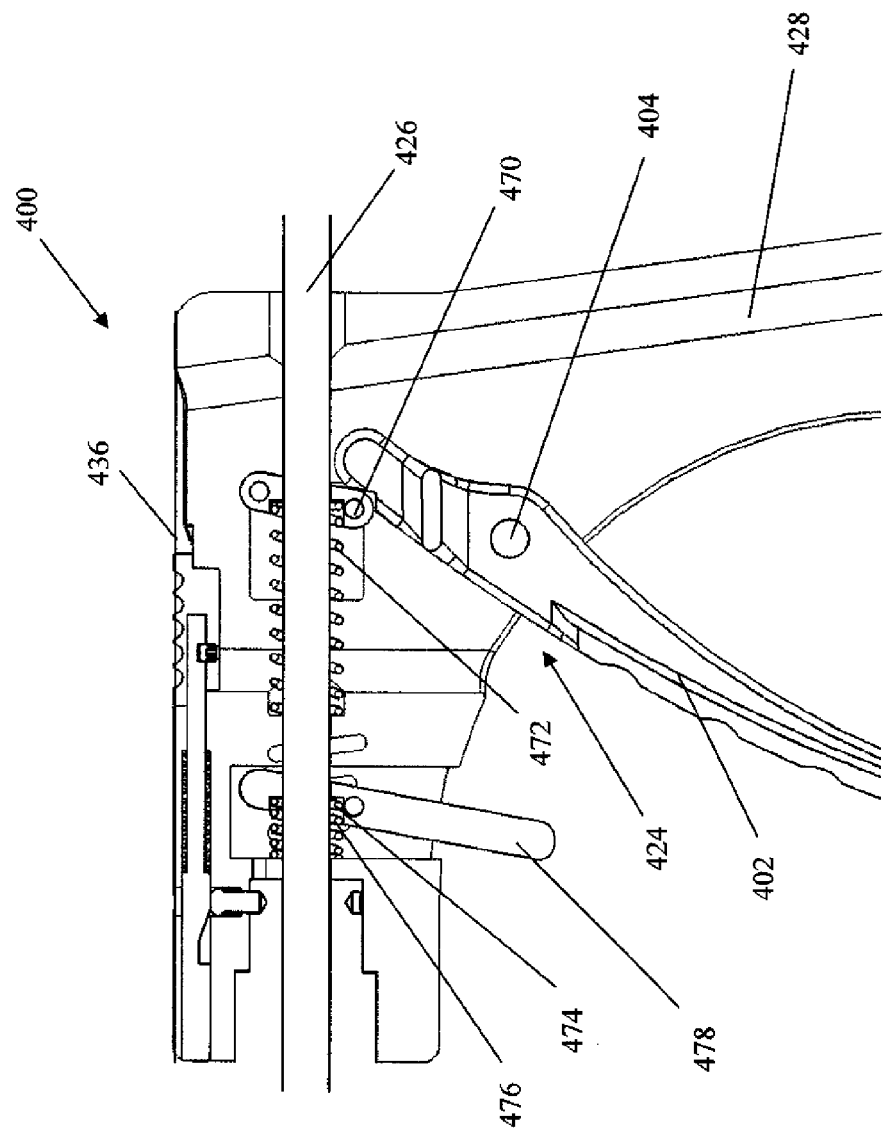

FIG. 4B shows a cutaway side view of the housing 436 of a non-ratcheting embodiment of the device 400. The first gripping spring 472 opposes the distal motion of the first gripping element 470 and the driving rod 426 that an operator causes by moving the activating lever 402 toward the handle 428. A second gripping spring 476 opposes proximal motion of the driving rod 426 when the lever 402 moves away from the handle 428. Movement of the lever 402 away from the handle 428 may be manually forced, or may be the result of an activating lever spring (not shown) within the handle 428 and attached to the activating lever pivot 404 which opposes movement of the lever 402 toward the handle 428. Also depicted is a gripping release lever 478, which is adapted to permit release the second gripping member 474 to allow the driving rod 426 to be retracted.

Some embodiments comprise a drive mechanism 424 comprising at least one gripping element 470 which opposes proximal motion of the drive mechanism 424. Activating the lever 402 drives the implant distally by moving the driving rod 426. As the activating lever 402 returns to its original position, the first gripping element 470 releases the driving rod 426, however the second gripping element 474 opposes proximal motion of the driving rod 426 and the implant. The drive mechanism may comprise a gripping spring 472, or 476, or two gripping springs 472 and 476.

In some embodiments of the distractor-inserter 400, the drive mechanism 424 comprises a gripping element 474 and a ratcheting drive mechanism as described previously. Some embodiments comprise other means for driving implant distally. These means can be other mechanical mechanisms capable of allowing unidirectional movement, along with a release mechanism for reversing such unidirectional movement. Some embodiments comprise other means for distracting the arms. The means for distracting may be other tools altogether through which the distractor-inserter may be placed and used to place the implant.

Figures 5, 6:
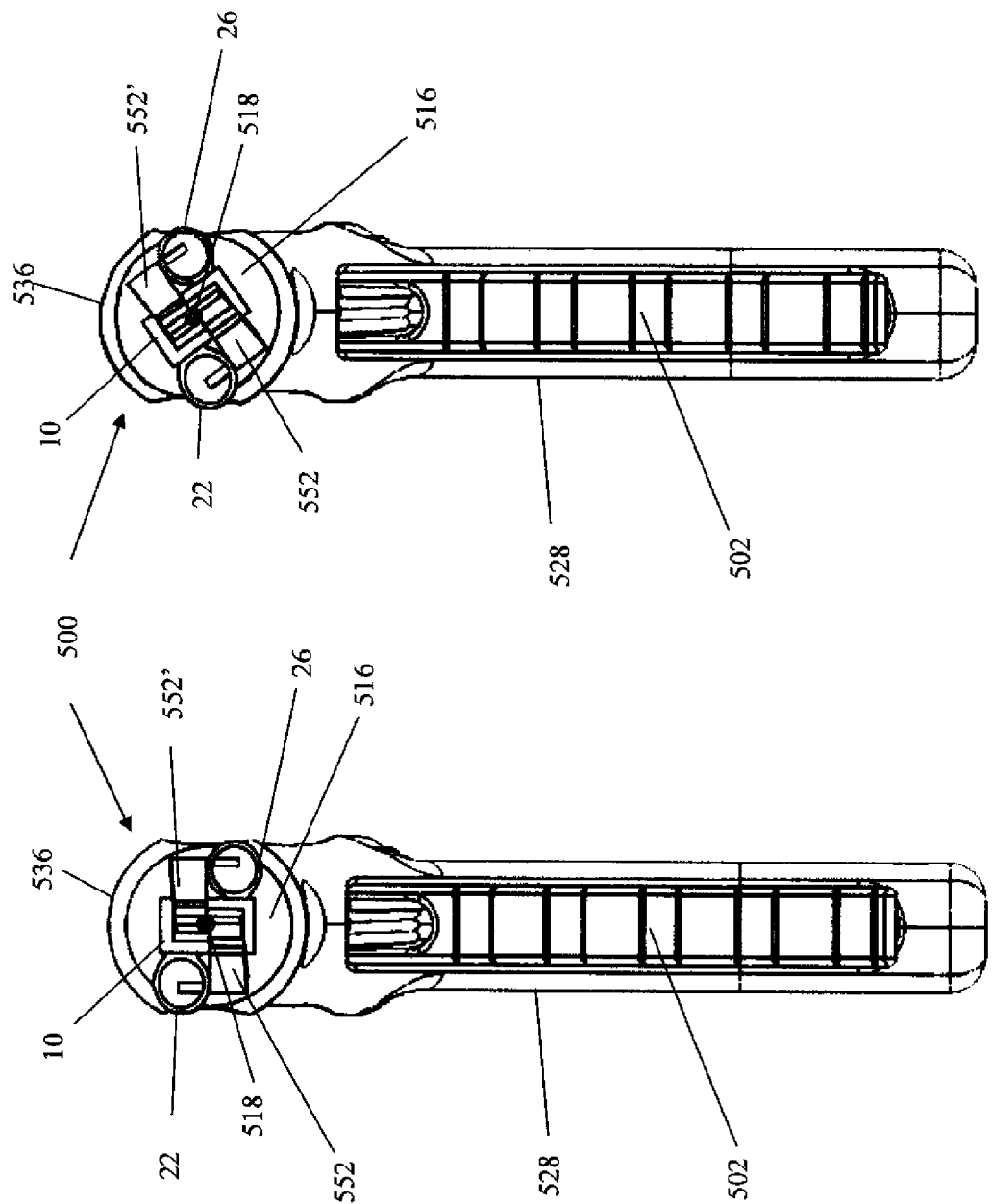
FIGS. 5 & 6 depict a frontal view of one embodiment of the device showing relative rotation of the arms in relation to the housing.

FIGS. 5 & 6 depict views of an embodiment of the device 500 showing relative rotation of the arms 552, 552' and the handle 528. Also shown in these views are the implant 10 and the activating lever 502. In use, the patient is stationary, and thus the arms 552, 552' of the device 500 and the implant 10 must remain in a fixed position relative to the patient during distraction and insertion for patient safety and for optimal implantation results. However, the user of the device 500 may need to be at a variety of angles relative to the patient; thus, the device is adapted to allow distraction and insertion in a more ergonomic manner for the user and, thus, a safer manner for the patient. This is achieved by allowing at least one degree of freedom of rotation in the device. That is, the device is adapted to allow for rotation of the handle 528, activating lever 502, and housing 536 relative to the arms 552, 552' and the implant 10, about the axis of the driving rod 526. This is achieved by providing at least one rotation element, such as a rotation disc that allows free rotation of these elements relative to each other.

FIG. 6 shows the axial view of the device 500 looking from the distal end to the proximal end of the device 500. In this view, the arms 552, 552' and implant 546, 546' are in a neutral position relative to the housing 536. In FIG. 6, also an axial view of the device 500 looking from the distal end to the proximal end of the device 500, the offset arms 552, 552' and implant depth guards 546, 546' are rotated relative to the housing 536 about the driving rod axis (shown as 518 for illustrative purposes only). A rotation element such as a rotation disc 516 may be present to rotate the housing around the arms 552, 552'. While it may appear that the arms 552, 552' are rotated, in use the rotation is relative, and the user will more likely rotate the housing 536 and the activating lever 502 relative to the arms 552, 552', keeping the arms 552, 552' and implant aligned appropriately with the vertebral anatomy of the patient.

In some embodiments, a vertebral distractor-inserter 500 comprises a pair of opposing arms 552, 552', a housing 536 in mechanical communication with the pair of laterally offset opposing arms 552, 552' and rotatable about an axis 518 extending between the pair of laterally offset opposing arms 552, 552', and a driving rod (not shown) extending through at least a portion of the housing 536 and between the pair of opposing arms 552, 552'. In addition to the housing 536 being rotatable around the pair of arms 552, 552', the handle 528 and the activating lever 502 are rotatable as well. In the depicted embodiments, the implant 10 is between the pair of opposing arms 552, 552' and the implant 10. Some embodiments further comprise a housing 536 comprising a housing rotation element 516, whereby the housing rotation element allows housing 536 and rod rotation relative to the pair of opposing arms 552, 552'.

In some embodiments, a vertebral distractor-inserter 500 comprises a pair of opposing arms 552, 552', a housing 536 in mechanical communication with the pair of opposing arms 552, 552' and rotatable about an axis 518 extending between the opposing arms 552, 552', a driving rod extending through at least a portion of the housing 536 and between the pair of opposing arms 552, 552', and a drive mechanism adapted to move the driving rod distally relative to the housing 536.

In some embodiments of a rotatable vertebral distractor-inserter 536, the vertebral distractor-inserter comprises a drive mechanism. Embodiments of the drive mechanism are described herein.

Figure 7A:
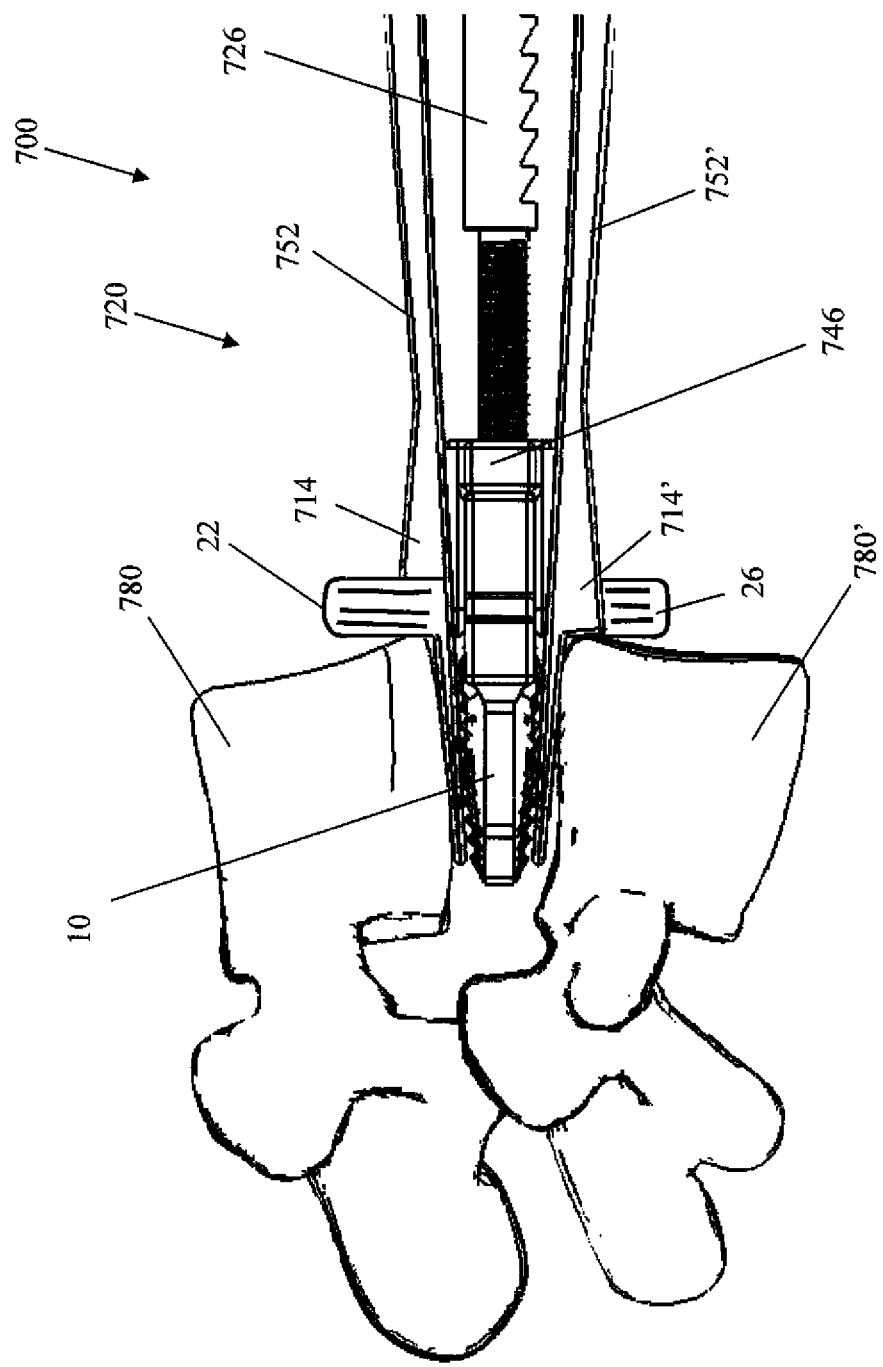
FIGS. 7A & 7B are views of one embodiment of the device in use.

FIG. 7A depicts a view of an embodiment of a device 700 in use showing distraction of adjacent vertebrae 780, 780'. Shown is the distal end 720 of a device 700 having opposing arms 752, 752', arm depth guards 714, 714', a driving rod 726 having an implant coupler 726. An implant 10 at the end of the driving rod 726 has flanges 22, 26. The implant 10 at the distal end of the implant coupler 746 has distracted the arms 752, 752' and is positioned between the vertebrae 780, 780'. The arm depth guards 714, 714' prevent the distractor from proceeding more than a predetermined depth into the intervertebral space. The flanges 22, 26 make contact with the vertebral bodies 780, 780', thereby limiting the depth to which the implant 10 may enter the intervertebral space.

Figure 7B:
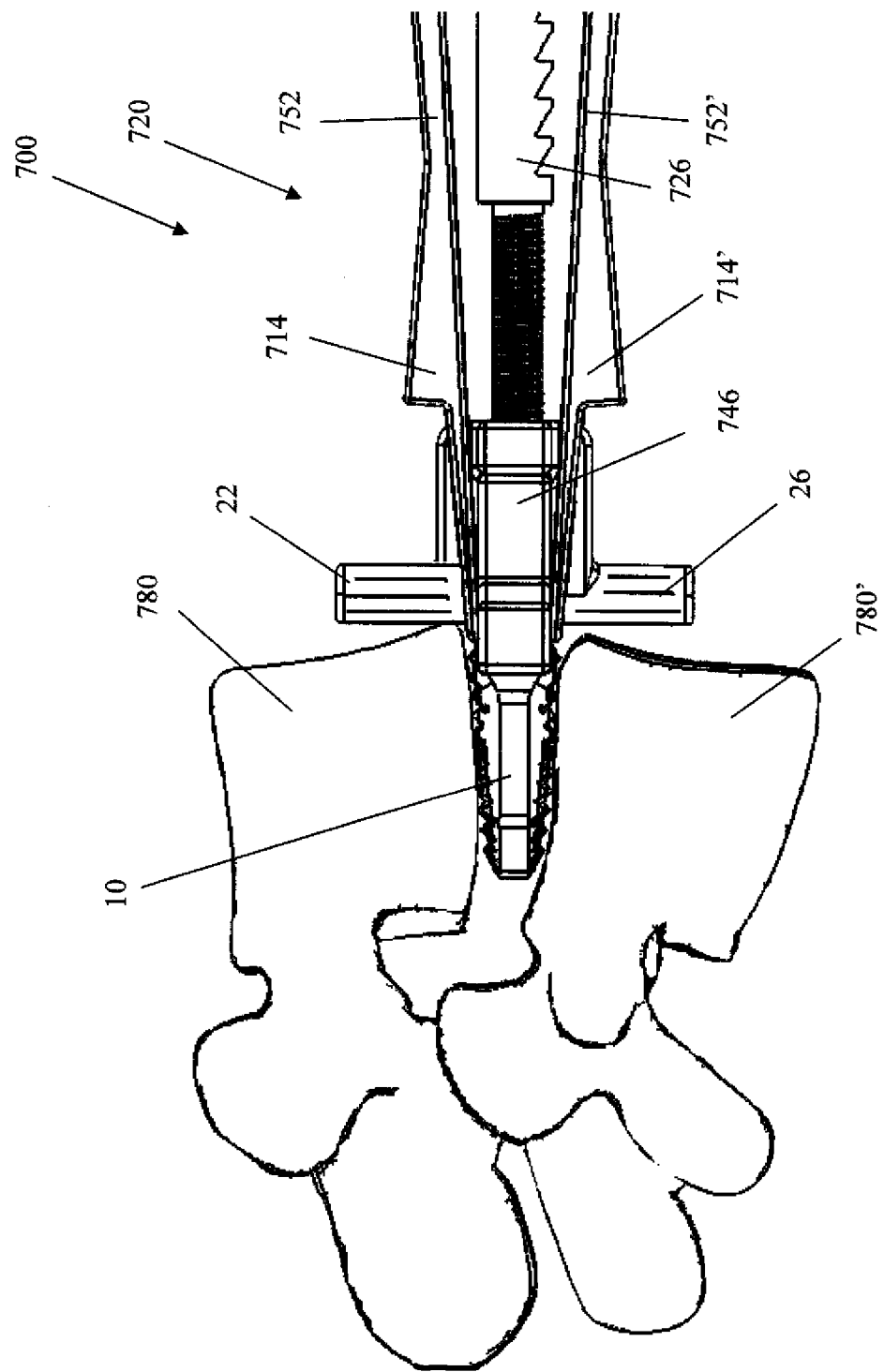

FIG. 7B depicts a view of an embodiment of the device 700 in use, showing insertion of an implant 10 between distracted vertebrae 780, 780' wherein the arms 752, 752' and the arm depth guards 714, 714' of the arms 752, 752' have been urged proximally out of the space between the vertebrae 780, 780', and the implant 10 is in direct contact with and sits between the vertebrae 780, 780'. The implant 780, 780' cannot move distally when the implant flanges 22, 26 abut the vertebrae 780, 780'. Further distal motion of the rod 726 relative to the device 700 results in the device 700 being pushed back from the vertebrae 780, 780', through the action of the flanges 22, 26, which are abutting the vertebrae 780, 780', and prevent further distal motion of the implant 10 into the intervertebral space.

The invention provides a method comprising inserting a flanged implant between a set of distracted vertebrae where a flanged implant is mounted to the driving rod of a vertebral distractor-inserter, where the vertebral distractor-inserter has a pair of laterally offset arms. The distal ends of the pair of offset opposing arms are then positioned between the adjacent vertebrae. The vertebrae are then distracted by preferably single-handed operation of the vertebral distractor-inserter. The flanged implant is moved distally by actuating a driving rod. The implant urges a pair of laterally offset arms apart, thereby imparting distraction force to a pair of adjacent vertebrae. The implant is then urged into the intervertebral space between the distracted vertebrae, preferably by single-handed operation of the vertebral distractor-inserter. At least one flange on the flanged implant engages an anterior surface of the vertebral body of at least one vertebra and pushes back on the distractor-inserter device. The pair of laterally offset opposing arms is then retracted from between the vertebrae by further distal motion of the driving rod.

In some embodiments, the method provides for a method of distracting adjacent vertebrae and inserting an implant between the distracted vertebrae where the vertebrae have been distracted with single-hand activation of the drive mechanism of the vertebral distractor-inserter. Activating the driving mechanism moves the implant distally, which distracts the pair of laterally offset opposing arms. The method also provides for distracting adjacent vertebrae and inserting a flanged implant between the distracted vertebrae by advancing the flanged implant into the distracted space between the vertebrae. The method further comprises a method for distracting adjacent vertebrae and inserting an implant between the distracted vertebrae by activating the driving mechanism with one hand and thereby extending the implant beyond the distal end of the pair of laterally offset opposing arms.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A vertebral distractor-inserter, comprising:
   (a) a pair of laterally offset opposing arms comprising a first arm having a proximal portion and a distal portion and a second arm having a proximal portion and a distal portion, wherein the pair of laterally offset opposing arms comprises a distracted configuration in which the distal portion of the first arm is separated from the distal portion of the second arm and a non-distracted configuration in which the distal portion of the first arm is adjacent to the distal portion of the second arm, wherein the distal portion of the first arm is laterally offset relative to the distal portion of the second arm, wherein the distal portion of the first arm is configured to cross the distal portion of the second arm;
   (b) a driving rod extending between the pair of laterally offset opposing arms; and
   (c) a drive mechanism in mechanical communication with the driving rod.

2. The distractor-inserter of claim 1, comprising a housing in mechanical communication with the pair of laterally offset opposing arms, wherein the driving rod extends through at least a portion of the housing.

3. The distractor-inserter of claim 2, comprising a handle attached to the housing.

4. The distractor-inserter of claim 2, wherein the drive mechanism is a ratchet drive mechanism.

5. The distractor-inserter of claim 4, wherein the ratchet drive mechanism comprises:
   (a) an activating lever mounted to the housing by an activating lever pivot;
   (b) the driving rod with a set of ratchet teeth on a surface of the driving rod;
   (c) a first ratchet pawl coupled to the activating lever and adapted to engage the set of ratchet teeth and move the driving rod distally relative to the housing; and (d) a second ratchet pawl adapted to engage the set of ratchet teeth and oppose proximal motion of the driving rod relative to the housing.

6. The distractor-inserter of claim 5, wherein the ratchet drive mechanism comprises an activating lever spring coupled to the activating lever and the handle, wherein the activating lever spring opposes proximal movement of the lever relative to the handle.

7. The distractor-inserter of claim 5, wherein the surface of the driving rod comprises an area that is substantially free of ratchet teeth on a contiguous lateral surface of the driving rod, and wherein the driving rod is movable proximally relative to the housing upon rotation of the rod about its axis such that the ratchet pawls are in contact with the contiguous lateral surface that is free of ratchet teeth.

8. The distractor-inserter of claim 7, wherein the ratchet teeth disengage from the first and second ratchet pawls upon rotation of the driving rod about its axis.

9. The distractor-inserter of claim 8, wherein the driving rod comprises a proximal end having a driving rod handle.

10. The distractor-inserter of claim 1, wherein the distractor-inserter is adapted for single-handed use.

11. The distractor-inserter of claim 1, wherein the driving rod comprises a distal end and an implant interface coupled to the distal end of the driving rod.

12. The distractor-inserter of claim 11, further comprising an implant in contact with the implant interface, whereby distal motion of the driving rod imparts distal motion to the implant through the implant interface; and distal motion of the implant forces the laterally offset opposing arms apart.

13. The distractor-inserter of claim 12, wherein the housing comprises an arm pivot.

14. The distractor-inserter of claim 13, wherein the pair of laterally offset opposing arms comprises an arm spring.

15. The distractor-inserter of claim 14, wherein at least one laterally offset opposing arm comprises an arm depth guard.

16. The distractor-inserter of claim 11, wherein the implant interface comprises an implant coupler.

17. The vertebral distractor-inserter of claim 1, wherein the driving rod comprises a distal end having an implant interface, and wherein the housing and at least a portion of the driving rod are rotatable relative to the pair of laterally offset opposing arms and the implant interface.

18. The vertebral distractor-inserter of claim 17, wherein the implant interface comprises an interface rotation element, whereby the interface rotation element allows rod rotation relative to the pair of laterally offset opposing arms.

19. The vertebral distractor-inserter of claim 18, wherein the housing comprises a housing rotation element, whereby the housing rotation element allows housing and rod rotation relative to the pair of laterally offset opposing arms.

20. A kit comprising:
(a) a vertebral distractor-inserter, comprising:
(i) a pair of opposing arms comprising a first arm having a proximal portion and a distal portion and a second arm having a proximal portion and a distal portion, wherein the opposing arms comprise a distracted configuration in which the distal portion of the first arm is separated from the distal portion of the second arm and a non-distracted configuration in which the distal portion of the first arm is adjacent to the distal portion of the second arm, wherein the distal portion of the first arm is laterally offset relative to the distal portion of the second arm, wherein the distal portion of the first arm is configured to cross the distal portion of the second arm;
(ii) a driving rod extending between the pair of opposing arms; and
(iii) a drive mechanism in mechanical communication with the driving rod; and
(b) a flanged vertebral implant comprising at least one flange.

21. The kit of claim 20, wherein the flanged vertebral implant comprises two flanges.

22. The kit of claim 21, wherein the flanged vertebral implant comprises two flanges having apertures in each.

23. The kit of claim 20, wherein the at least one flange has an aperture therein.

* * * * *

UNITED STATES PATENT AND TRADEMARK OFFICE
CERTIFICATE OF CORRECTION

| | | |
|---|---|---|
| PATENT NO. | : 8,864,770 B2 | Page 1 of 1 |
| APPLICATION NO. | : 12/047178 | |
| DATED | : October 21, 2014 | |
| INVENTOR(S) | : Jason Daniel Blain | |

It is certified that error appears in the above-identified patent and that said Letters Patent is hereby corrected as shown below:

On The Title Page (item 74, Attorney) at line 1, Change "Marten," to --Martens,--.

In The Specification

In column 15 at line 36, Change "312" to --372--.

Signed and Sealed this
Fifth Day of May, 2015

Michelle K. Lee
*Director of the United States Patent and Trademark Office*